US012735453B2

(12) United States Patent
Khalaila et al.

(10) Patent No.: US 12,735,453 B2
(45) Date of Patent: Sep. 15, 2026

(54) DELIVERY PEPTIDES AND METHODS OF USING THE SAME

(71) Applicants: NATIONAL INSTITUTE FOR BIOTECHNOLOGY IN THE NEGEV LTD., Beer-Sheva (IL); B. G. NEGEV TECHNOLOGIES AND APPLICATIONS LTD., Beer-Sheva (IL)

(72) Inventors: Isam Khalaila, Beer-Sheva (IL); Amir Sagi, Omer (IL); Shany Cohen, Givataim (IL)

(73) Assignees: NATIONAL INSTITUTE FOR BIOTECHNOLOGY IN THE NEGEV LTD., Beer-Sheva (IL); B. G. NEGEV TECHNOLOGIES AND APPLICATIONS LTD., Beer-Sheva (IL)

( * ) Notice: Subject to any disclaimer, the term of this patent is extended or adjusted under 35 U.S.C. 154(b) by 799 days.

(21) Appl. No.: 17/671,974

(22) Filed: Feb. 15, 2022

(65) Prior Publication Data

US 2022/0204563 A1 Jun. 30, 2022

Related U.S. Application Data

(63) Continuation of application No. PCT/IL2020/050897, filed on Aug. 13, 2020.

(60) Provisional application No. 62/887,050, filed on Aug. 15, 2019.

(51) Int. Cl.
*C07K 7/08* (2006.01)
*C07K 19/00* (2006.01)

(52) U.S. Cl.
CPC ................ *C07K 7/08* (2013.01); *C07K 19/00* (2013.01); *C07K 2317/24* (2013.01)

(58) Field of Classification Search
None
See application file for complete search history.

(56) References Cited

U.S. PATENT DOCUMENTS 5,932,447 A 8/1999 Siegall

FOREIGN PATENT DOCUMENTS

| | | | | |
|---|---|---|---|---|
| CN | 111171131 A | 5/2020 | | |
| WO | 2007095152 A2 | 8/2007 | | |
| WO | 2008118212 A2 | 10/2008 | | |
| WO | WO-2009046220 A2 * | 4/2009 | .......... | A61K 31/713 |
| WO | 2009081154 A1 | 7/2009 | | |
| WO | 2010105277 A1 | 9/2010 | | |
| WO | 2010129023 A2 | 11/2010 | | |
| WO | 2013096958 A1 | 6/2013 | | |
| WO | 2019089452 A1 | 5/2019 | | |

OTHER PUBLICATIONS

Cohen et al. A crustacean vitellogeninderived peptide as an oocyte-specific delivery vehicle for gene silencing. Front. Mar. Sci. (2023) 10:1128524. doi: 10.3389/fmars.2023.1128524 (Year: 2023).*
Margus et al. Characteristics of Cell-Penetrating Peptide/Nucleic Acid Nanoparticles. Molecular Pharmaceutics 2016 13 (1), 172-179, DOI: 10.1021/acs.molpharmaceut.5b00598 (Year: 2016).*
Numata et al. Local gene silencing in plants via synthetic dsRNA and carrier peptide. Plant Biotechnol. J. 2014, 12, 1027-1034 (Year: 2014).*
Li A, Sadasivam M, Ding JL. Receptor-ligand interaction between vitellogenin receptor (VtgR) and vitellogenin (Vtg), implications on low density lipoprotein receptor and apolipoprotein B/E. The first three ligand-binding repeats of VtgR interact with the amino-terminal region of Vtg. J Biol Chem. Jan. 31, 2003;278(5):2799-806. doi: 10.1074/jbc.M205067200. Epub Nov. 11, 2002. PMID: 12429745.
Chaverra-Rodriguez D, Macias VM, Hughes GL, Pujhari S, Suzuki Y, Peterson DR, Kim D, McKeand S, Rasgon JL. Targeted delivery of CRISPR-Cas9 ribonucleoprotein into arthropod ovaries for heritable germline gene editing. Nat Commun. Aug. 1, 2018;9(1):3008. doi: 10.1038/s41467-018-05425-9. PMID: 30068905; PMCID: PMC6070532.
Roth Z, Khalaila I. Identification and characterization of the vitellogenin receptor in Macrobrachium rosenbergii and its expression during vitellogenesis. Mol Reprod Dev. Jul. 2012;79(7):478-87. doi: 10.1002/mrd.22055. PMID: 22674884.
Roth Z, Weil S, Aflalo ED, Manor R, Sagi A, Khalaila I. Identification of receptor-interacting regions of vitellogenin within evolutionarily conserved β-sheet structures by using a peptide array. Chembiochem. Jun. 17, 2013;14(9):1116-22. doi: 10.1002/cbic.201300152. Epub Jun. 3, 2013. PMID: 23733483.
Rungger D, Muster L, Georgiev O, Rungger-Brändle E. Oocyte shuttle, a recombinant protein transporting donor DNA into the Xenopus oocyte in situ. Biol Open. Feb. 15, 2017;6(2):290-295. doi: 10.1242/bio.022376. PMID: 28202471; PMCID: PMC5312104.
PCT Search Report for International Application No. PCT/IL2020/050897 mailed Nov. 20, 2020, 4 pp.
PCT Written Opinion for International Application No. PCT/IL2020/050897 mailed Nov. 20, 2020, 4 pp.
PCT Preliminary Examination Report on Patentability for International Application No. PCT/IL2020/050897 dated Feb. 8, 2022, 5 pp.
Pirkle and McKendry, Internal Photoaddtion Reactions of 2-Pyrone and N-Methyl-2-pyridone: A New Synthetic Approach to Cyclobutadiene, Journal of the American Chemical Society, 1964, Soc, 85:2149, https://doi.org/10.1021/ia01059a059.
Cohen et al., A crustacean vitellogenin-derived peptide as an oocyte-specific delivery vehicle for gene silencing, Frontiers in Marine Science, vol. 10, Mar. 16, 2023, DOI: 10.3389/fmars.2023.1128524.
Ziv Roth et al., "Identification of Receptor-Interacting Regions of Vitellogenin within Evolutionarily Conserved b-Sheet Structures by Using a Peptide Array", ChemBioChem 2013, 14, 1116-1122. doi: 10.1002/cbic.201300152. Epub Jun. 3, 2013. PMID: 23733483.

(Continued)

*Primary Examiner* — Christina Bradley
(74) *Attorney, Agent, or Firm* — The Roy Gross Law Firm, LLC; Roy D. Gross

(57) ABSTRACT

The present invention is directed to a peptide, and methods of using the same such as in the delivery of an agent into a cell, or modification of a cell.

7 Claims, 10 Drawing Sheets
(3 of 10 Drawing Sheet(s) Filed in Color)

Specification includes a Sequence Listing.

(56) References Cited

OTHER PUBLICATIONS

Dripps et al., "Interleukin-1 (IL-1) receptor antagonist binds to the 80-kDa IL-1 receptor but does not initiate IL-1 signal transduction" (1991); The Journal of Biological Chemistry 266(16): 10331-10336.
Snigirevskaya et al., "Internalization and recycling of vitellogenin receptor in the mosquito oocyte", Cell Tissue Res (1997) 290:175-183.

* cited by examiner

12$\mu$M 6$\mu$M 1.5$\mu$M 0.75$\mu$M

Vg-

OverlayscVg-

Overlay-

**Vg-ds*PAX6* scVg-ds*PAX6***
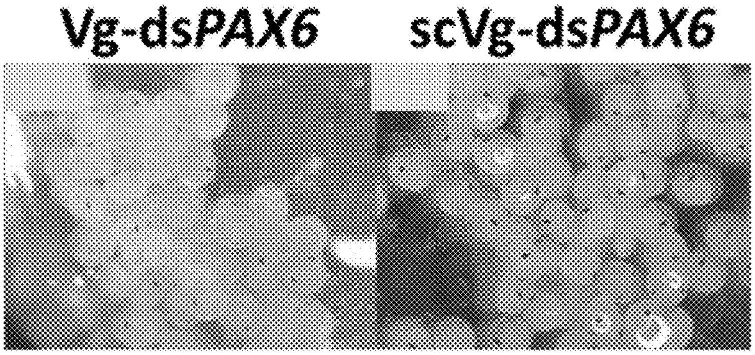
FIGURE 7A-I FIGURE 7A-VI
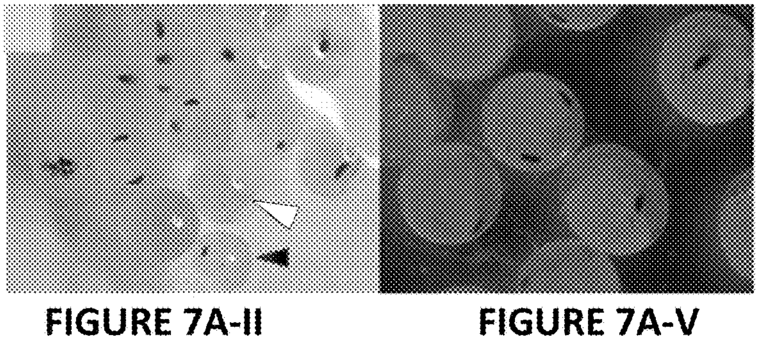
FIGURE 7A-II FIGURE 7A-V
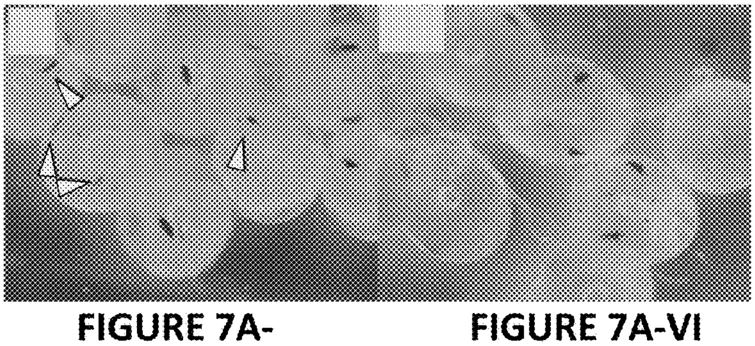
FIGURE 7A-III FIGURE 7A-VI
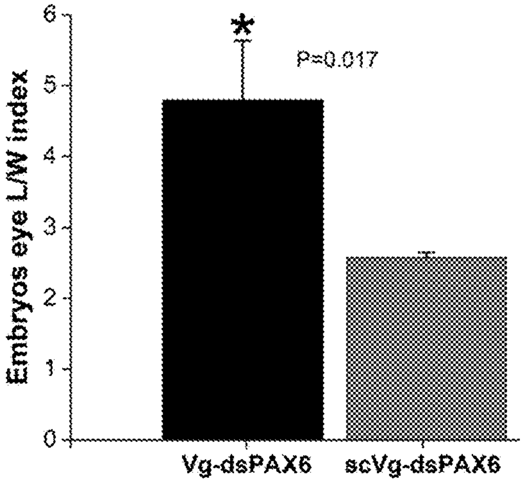
FIGURE 7B
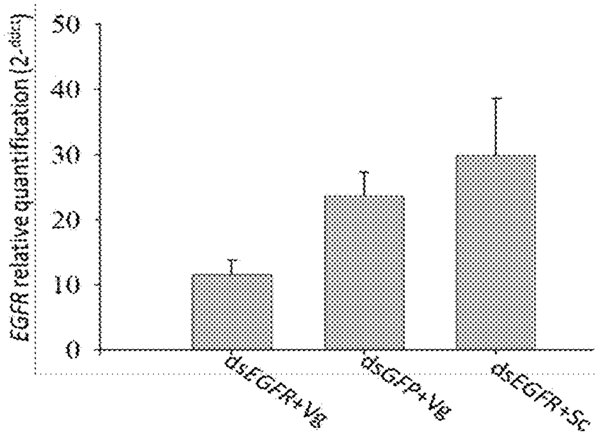
FIGURE 7C

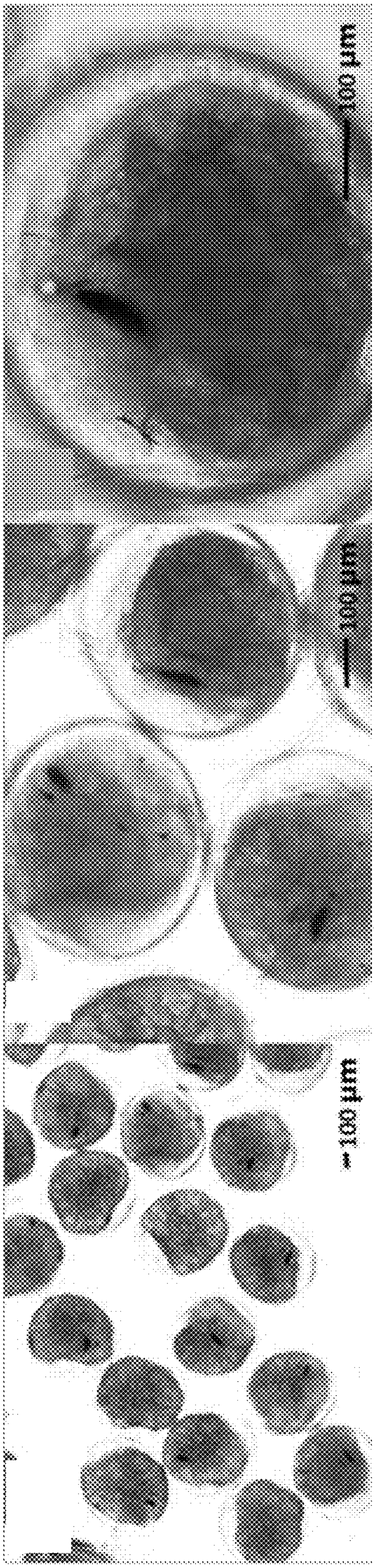
FIGURE 8A-I FIGURE 8A-II FIGURE 8A-III
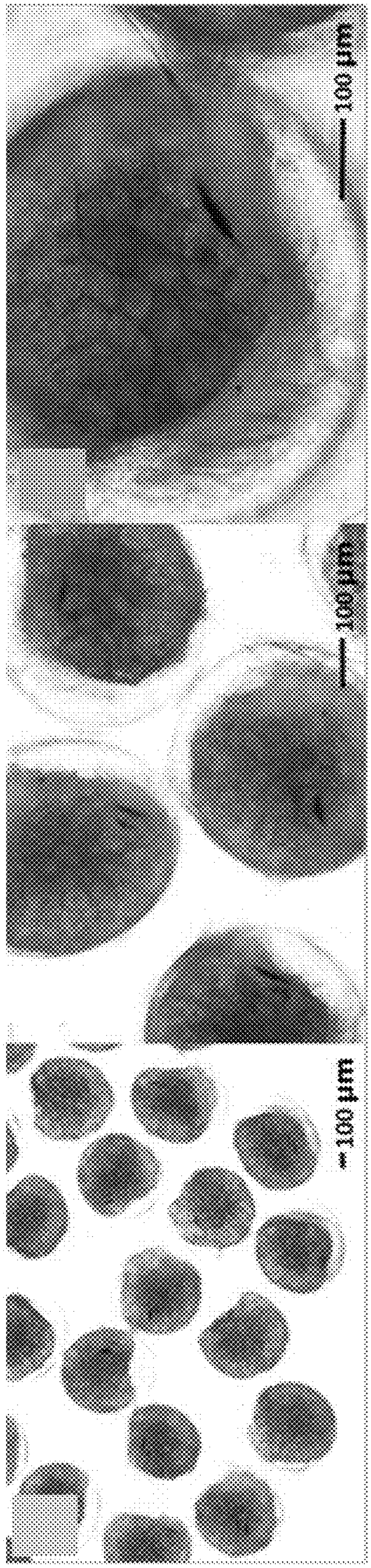
FIGURE 8A-IV FIGURE 8A-V FIGURE 8A-VI

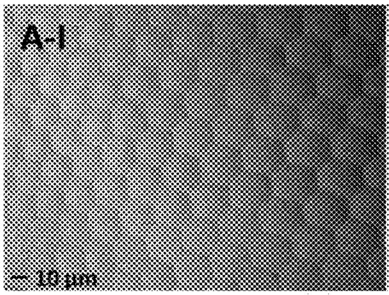
FIGURE 9A-I
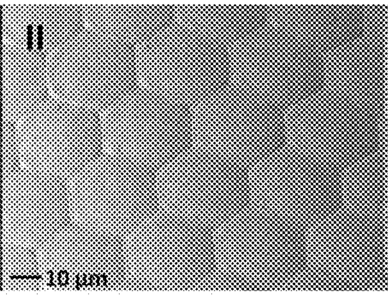
FIGURE 9A-II
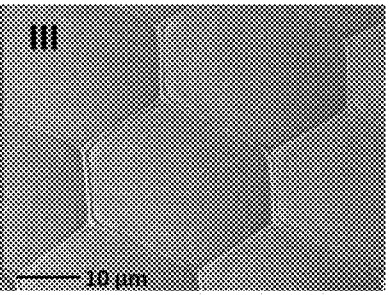
FIGURE 9A-III
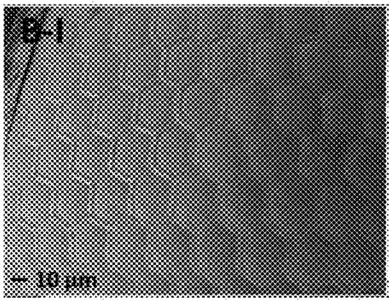
FIGURE 9B-I
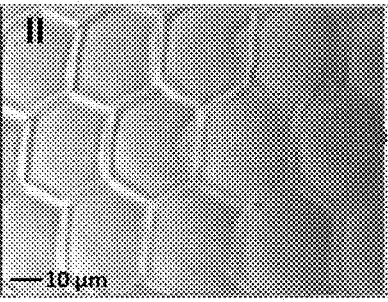
FIGURE 9B-II
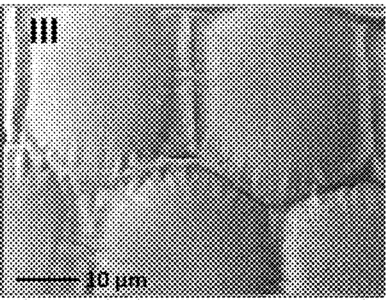
FIGURE 9B-III
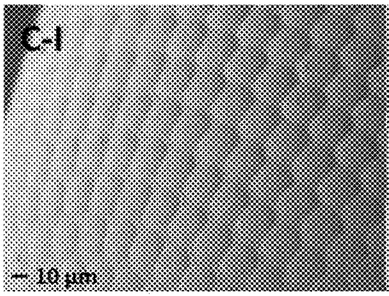
FIGURE 9C-I
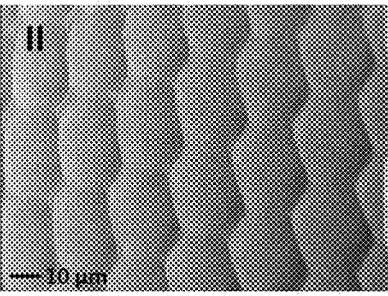
FIGURE 9C-II
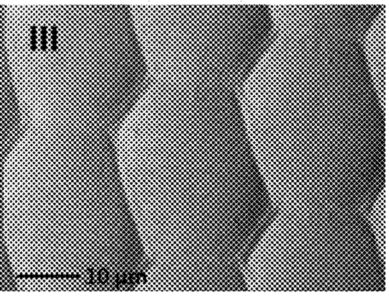
FIGURE 9C-III
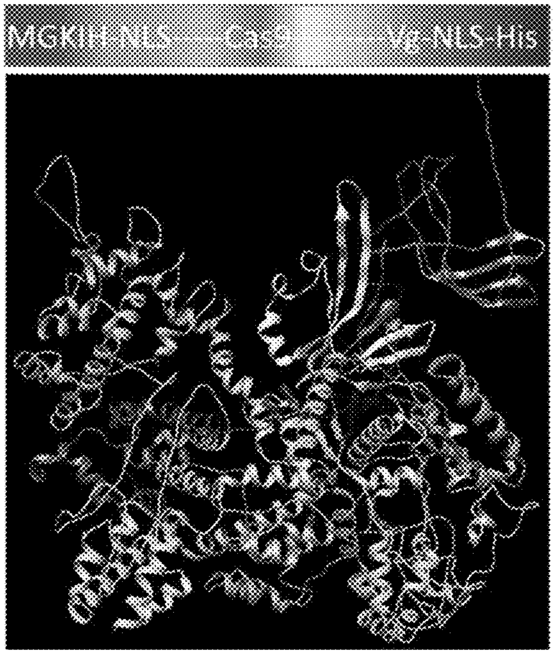
FIGURE 10A

| Species | ID | Location | Sequence | | | | | | | | | | | | | | | | | | | | | | | | | |
|---|---|---|---|---|---|---|---|---|---|---|---|---|---|---|---|---|---|---|---|---|---|---|---|---|---|---|---|---|
| *M. rosenbergii* | BAB69831.1 | 235-260 | C | K | D | K | N | I | I | K | P | A | Y | G | S | Y | K | Y | V | E | A | H | Q | E | S | V | L | R |
| | | | | + | | | N | I | + | + | | A | | | | | | | | | | | Q | + | | | L | R |
| *L. vannamei* | AAP76871.2 | 236-261 | | Q | | | N | I | V | R | | A | I | | I | | | | | | | S | Q | D | | Y | L | R |
| *P. monodon* | ABB86953.1 | 236-261 | | Q | | | N | I | V | R | | A | I | | I | | | | | | | S | Q | D | | Y | L | R |
| | | | C | + | D | K | N | + | + | K | P | + | Y | G | + | Y | K | Y | V | E | A | | | | S | | L | + |
| *C. quadricarinatus* | AAG17936.1 | 236-261 | C | E | D | K | N | V | V | K | P | S | Y | G | A | Y | K | Y | V | E | A | K | M | M | S | T | L | K |
| | | | | + | | | | + | I | K | | + | Y | | + | | | | | | | | Q | E | | | + | + |
| *C. sapidus* | ABC41825.1 | 235-260 | | E | | | K | V | I | K | | S | Y | | I | | | | | | | K | Q | E | | T | M | K |
| | | | | + | | | | + | + | + | | A | Y | | + | | | + | | | | | Q | E | | | L | R |
| *E. sinensis* | QBO55679.1 | 235-260 | | E | | | K | V | V | R | | A | Y | | T | | | | | | | E | Q | E | | T | L | R |
| | | | C | | D | K | | + | + | + | P | + | Y | G | + | Y | K | Y | V | E | A | | Q | E | S | | L | R |
| *H. americanus* | ABO08883.1 | 237-262 | C | H | D | K | K | V | V | R | P | S | Y | G | A | Y | K | Y | V | E | A | K | Q | E | S | T | L | R |

FIGURE 11A

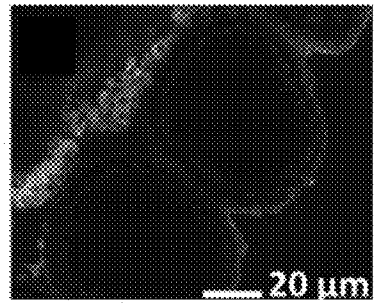

FIGURE 11B

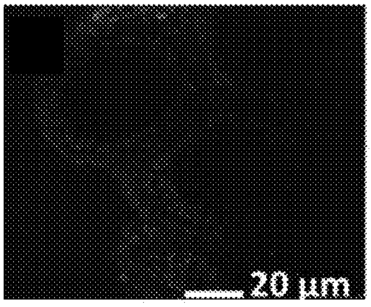

FIGURE 11C

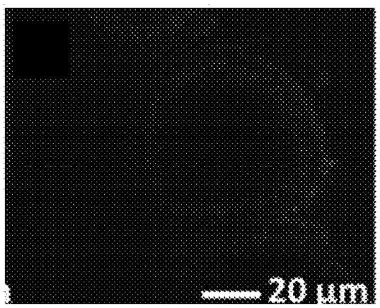

FIGURE 11D

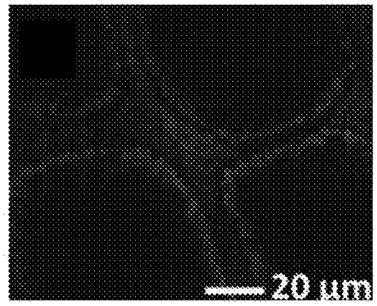

FIGURE 11E

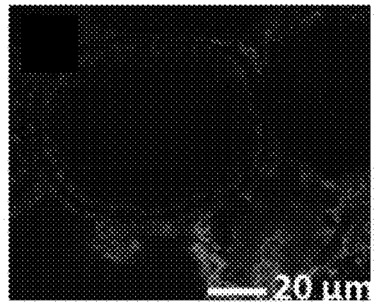

FIGURE 11F

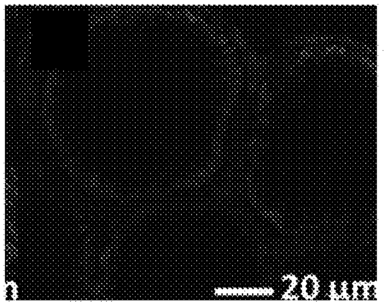

FIGURE 11G

SEQUENCE LISTING

```
<160> NUMBER OF SEQ ID NOS: 42

<210> SEQ ID NO 1
<211> LENGTH: 23
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
```

```
<223> OTHER INFORMATION: X is Asn or Lys
<220> FEATURE:
<221> NAME/KEY: MISC_FEATURE
<222> LOCATION: (4)..(5)
<223> OTHER INFORMATION: X is Ile or Val
<220> FEATURE:
<221> NAME/KEY: MISC_FEATURE
<222> LOCATION: (6)..(6)
<223> OTHER INFORMATION: X is Lys or Arg
<220> FEATURE:
<221> NAME/KEY: MISC_FEATURE
<222> LOCATION: (8)..(8)
<223> OTHER INFORMATION: X is Ala or Ser
<220> FEATURE:
<221> NAME/KEY: MISC_FEATURE
<222> LOCATION: (9)..(9)
<223> OTHER INFORMATION: X is Tyr or Ile
<220> FEATURE:
<221> NAME/KEY: MISC_FEATURE
<222> LOCATION: (11)..(11)
<223> OTHER INFORMATION: X is Ser, Ile, Ala, or Thr
<220> FEATURE:
<221> NAME/KEY: MISC_FEATURE
<222> LOCATION: (18)..(18)
<223> OTHER INFORMATION: X is His, Ser, Lys, or Glu
<220> FEATURE:
<221> NAME/KEY: MISC_FEATURE
<222> LOCATION: (19)..(19)
<223> OTHER INFORMATION: X is Gln or Met
<220> FEATURE:
<221> NAME/KEY: MISC_FEATURE
<222> LOCATION: (20)..(20)
<223> OTHER INFORMATION: X is Glu, Asp, or Met
<220> FEATURE:
<221> NAME/KEY: MISC_FEATURE
<222> LOCATION: (22)..(22)
<223> OTHER INFORMATION: X is Val or Thr
<220> FEATURE:
<221> NAME/KEY: MISC_FEATURE
<222> LOCATION: (23)..(23)
<223> OTHER INFORMATION: X is Leu or Met

<400> SEQUENCE: 1

Asp Lys Xaa Xaa Xaa Xaa Pro Xaa Xaa Gly Xaa Tyr Lys Tyr Val Glu
1               5                   10                  15

Ala Xaa Xaa Xaa Ser Xaa Xaa
            20


<210> SEQ ID NO 2
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is Asn or Lys
<220> FEATURE:
<221> NAME/KEY: MISC_FEATURE
<222> LOCATION: (4)..(5)
<223> OTHER INFORMATION: X is Ile or Val
<220> FEATURE:
<221> NAME/KEY: MISC_FEATURE
<222> LOCATION: (6)..(6)
<223> OTHER INFORMATION: X is Lys or Arg
<220> FEATURE:
<221> NAME/KEY: MISC_FEATURE
<222> LOCATION: (8)..(8)
<223> OTHER INFORMATION: X is Ala or Ser
<220> FEATURE:
<221> NAME/KEY: MISC_FEATURE
<222> LOCATION: (9)..(9)
<223> OTHER INFORMATION: X is Tyr or Ile
<220> FEATURE:
<221> NAME/KEY: MISC_FEATURE
```

<222> LOCATION: (11)..(11)
<223> OTHER INFORMATION: X is Ser, Ile, Ala, or Thr

<400> SEQUENCE: 2

Asp Lys Xaa Xaa Xaa Xaa Pro Xaa Xaa Gly Xaa Tyr Lys Tyr Val Glu
1 5 10 15

Ala

<210> SEQ ID NO 3
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is Asn or Lys
<220> FEATURE:
<221> NAME/KEY: MISC_FEATURE
<222> LOCATION: (4)..(5)
<223> OTHER INFORMATION: X is Ile or Val
<220> FEATURE:
<221> NAME/KEY: MISC_FEATURE
<222> LOCATION: (6)..(6)
<223> OTHER INFORMATION: X is Lys or Arg
<220> FEATURE:
<221> NAME/KEY: MISC_FEATURE
<222> LOCATION: (8)..(8)
<223> OTHER INFORMATION: X is Ala or Ser

<400> SEQUENCE: 3

Asp Lys Xaa Xaa Xaa Xaa Pro Xaa
1 5

<210> SEQ ID NO 4
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is Ans or Lys
<220> FEATURE:
<221> NAME/KEY: MISC_FEATURE
<222> LOCATION: (4)..(5)
<223> OTHER INFORMATION: X is Ile or Val
<220> FEATURE:
<221> NAME/KEY: MISC_FEATURE
<222> LOCATION: (6)..(6)
<223> OTHER INFORMATION: X is Lys or Arg

<400> SEQUENCE: 4

Asp Lys Xaa Xaa Xaa Xaa Pro
1 5

<210> SEQ ID NO 5
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is Ser, Ile, Ala, or Thr

<400> SEQUENCE: 5

Gly Xaa Tyr Lys Tyr Val Glu Ala 1 5

<210> SEQ ID NO 6
<211> LENGTH: 17
<212> TYPE: PRT
<213> ORGANISM: Artificial Sequence
<220> FEATURE:
<223> OTHER INFORMATION: Synthetic

<400> SEQUENCE: 6

Asp Lys Asn Ile Ile Lys Pro Ala Tyr Gly Ser Tyr Lys Tyr Val Glu
1 5 10 15

Ala

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

Asp Lys Asn Ile Ile Lys Pro
1 5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Asp Lys Asn Ile Val Arg Pro Ala
1 5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Gly Ser Tyr Lys Tyr Val Glu Ala
1 5

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Gly Ile Tyr Lys Tyr Val Glu Ala
1 5

<210> SEQ ID NO 11
<211> LENGTH: 18
<212> TYPE: PRT
<213> ORGANISM: Artificial Sequence
<220> FEATURE:
<223> OTHER INFORMATION: Synthetic

<400> SEQUENCE: 11

-continued

```
Lys His Lys His Lys His Lys His Lys His Lys His Lys His Lys His
1               5                   10                  15

Lys His


<210> SEQ ID NO 12
<211> LENGTH: 16
<212> TYPE: PRT
<213> ORGANISM: Artificial Sequence
<220> FEATURE:
<223> OTHER INFORMATION: Synthetic

<400> SEQUENCE: 12

Lys His Lys His Lys His Lys His Lys His Lys His Lys His Lys His
1               5                   10                  15


<210> SEQ ID NO 13
<211> LENGTH: 14
<212> TYPE: PRT
<213> ORGANISM: Artificial Sequence
<220> FEATURE:
<223> OTHER INFORMATION: Synthetic

<400> SEQUENCE: 13

Lys His Lys His Lys His Lys His Lys His Lys His Lys His
1               5                   10


<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

Lys His Lys His Lys His Lys His Lys His Lys His
1               5                   10


<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Lys His Lys His Lys His Lys His Lys His
1               5                   10


<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Lys His Lys His Lys His Lys His
1               5


<210> SEQ ID NO 17
<211> LENGTH: 6
<212> TYPE: PRT
<213> ORGANISM: Artificial Sequence
<220> FEATURE:
<223> OTHER INFORMATION: Synthetic

<400> SEQUENCE: 17
```

-continued

Lys His Lys His Lys His
1 5

<210> SEQ ID NO 18
<211> LENGTH: 4
<212> TYPE: PRT
<213> ORGANISM: Artificial Sequence
<220> FEATURE:
<223> OTHER INFORMATION: Synthetic

<400> SEQUENCE: 18

Lys His Lys His
1

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Lys Lys Lys Lys Lys Lys Lys Lys Lys
1 5

<210> SEQ ID NO 20
<211> LENGTH: 66
<212> TYPE: PRT
<213> ORGANISM: Artificial Sequence
<220> FEATURE:
<223> OTHER INFORMATION: Synthetic

<400> SEQUENCE: 20

Pro Val Ser Leu Leu Gln Glu Leu Cys Met Arg Arg Gly Ile Ser Pro
1 5 10 15

Lys Tyr Asp Leu Leu Gln Ile Glu Gly Ala Val His Glu Pro Thr Phe
20 25 30

Val Tyr Arg Val Thr Val Gly Glu Phe Ala Ala Asn Gly Ser Gly Gln
35 40 45

Ser Lys Lys Lys Ala Lys His Ala Ala Ala Lys Ala Val Leu Asp Ile
50 55 60

Ile Ile
65

<210> SEQ ID NO 21
<211> LENGTH: 1390
<212> TYPE: PRT
<213> ORGANISM: Artificial Sequence
<220> FEATURE:
<223> OTHER INFORMATION: Synthetic

<400> SEQUENCE: 21

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

-continued

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495
```

-continued

```
Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
```

-continued

```
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320
```

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

Gly Gly Ser Gly Pro Pro Lys Lys Lys Arg Lys Val Tyr Pro Tyr
1370 1375 1380

Asp Val Pro Asp Tyr Ala Cys
1385 1390

<210> SEQ ID NO 22
<211> LENGTH: 26
<212> TYPE: PRT
<213> ORGANISM: Artificial Sequence
<220> FEATURE:
<223> OTHER INFORMATION: Synthetic

<400> SEQUENCE: 22

Cys Asp Lys Asn Ile Ile Lys Pro Ala Tyr Gly Ser Tyr Lys Tyr Val
1 5 10 15

Glu Ala His Gln Glu Ser Val Leu Arg Lys
20 25

<210> SEQ ID NO 23
<211> LENGTH: 26
<212> TYPE: PRT
<213> ORGANISM: Artificial Sequence
<220> FEATURE:
<223> OTHER INFORMATION: Synthetic

<400> SEQUENCE: 23

Cys Gln Ala Pro Val Lys Leu Ile Ala Tyr Asp Lys Asn Lys Tyr Glu
1 5 10 15

His Glu Tyr Arg Ile Ser Val Ser Gly Lys
20 25

<210> SEQ ID NO 24
<211> LENGTH: 44
<212> TYPE: PRT
<213> ORGANISM: Artificial Sequence
<220> FEATURE:
<223> OTHER INFORMATION: Synthetic

<400> SEQUENCE: 24

Lys His Lys His Lys His Lys His Lys His Lys His Lys His Lys His
1 5 10 15

Lys His Cys Asp Lys Asn Ile Ile Lys Pro Ala Tyr Gly Ser Tyr Lys
20 25 30

Tyr Val Glu Ala His Gln Glu Ser Val Leu Arg Lys
35 40

<210> SEQ ID NO 25
<211> LENGTH: 44
<212> TYPE: PRT
<213> ORGANISM: Artificial Sequence
<220> FEATURE:
<223> OTHER INFORMATION: Synthetic

<400> SEQUENCE: 25

Lys His Lys His Lys His Lys His Lys His Lys His Lys His Lys His
1 5 10 15

```
Lys His Cys Gln Ala Pro Val Lys Leu Ile Ala Tyr Asp Lys Asn Lys
            20                  25                  30

Tyr Glu His Glu Tyr Arg Ile Ser Val Ser Gly Lys
        35                  40


<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26

atggtgagca agggcgagga                                                  20


<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27

ttacttgtac agctcgtcca t                                                21


<210> SEQ ID NO 28
<211> LENGTH: 23
<212> TYPE: DNA
<213> ORGANISM: Artificial Sequence
<220> FEATURE:
<223> OTHER INFORMATION: Synthetic

<400> SEQUENCE: 28

gaaagatagt ggtgcctgcg tta                                              23


<210> SEQ ID NO 29
<211> LENGTH: 23
<212> TYPE: DNA
<213> ORGANISM: Artificial Sequence
<220> FEATURE:
<223> OTHER INFORMATION: Synthetic

<400> SEQUENCE: 29

cttttcccca gcaaccttca tta                                              23


<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30

gactggctgc aaagataggc                                                  20


<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31

gcctgccata gacccataag                                                  20
```

-continued

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
tgggtcgaga ccattctcat 20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
agagaagacc ggcttgtgaa 20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
taatacgact cactataggg 20

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
gaaagaaaat acgctcacct tg 22

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
agtcacctct tggacgttgc 20

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Asp Lys Asn Ile Ile Lys Pro Lys
1 5

<210> SEQ ID NO 38
<211> LENGTH: 9
<212> TYPE: PRT
<213> ORGANISM: Artificial Sequence
<220> FEATURE:

-continued

```
<223> OTHER INFORMATION: Synthetic

<400> SEQUENCE: 38

Gly Ser Tyr Lys Tyr Val Glu Ala Lys
1               5


<210> SEQ ID NO 39
<211> LENGTH: 18
<212> TYPE: PRT
<213> ORGANISM: Artificial Sequence
<220> FEATURE:
<223> OTHER INFORMATION: Synthetic

<400> SEQUENCE: 39

Asp Lys Asn Ile Ile Lys Pro Ala Tyr Gly Ser Tyr Lys Tyr Val Glu
1               5                   10                  15

Ala Lys


<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Asp Lys Asn Ile Val Arg Pro Ala Lys
1               5


<210> SEQ ID NO 41
<211> LENGTH: 9
<212> TYPE: PRT
<213> ORGANISM: Artificial Sequence
<220> FEATURE:
<223> OTHER INFORMATION: Synthetic

<400> SEQUENCE: 41

Gly Ile Tyr Lys Tyr Val Glu Ala Lys
1               5


<210> SEQ ID NO 42
<211> LENGTH: 23
<212> TYPE: PRT
<213> ORGANISM: Artificial Sequence
<220> FEATURE:
<223> OTHER INFORMATION: Synthetic

<400> SEQUENCE: 42

Asp Lys Asn Ile Ile Lys Pro Ala Tyr Gly Ser Tyr Lys Tyr Val Glu
1               5                   10                  15

Ala His Gln Glu Ser Val Leu
            20
```

DELIVERY PEPTIDES AND METHODS OF USING THE SAME

CROSS-REFERENCE TO RELATED APPLICATIONS

This application is a Bypass Continuation of PCT Patent Application No. PCT/IL2020/050897 having International Filing date of Aug. 13, 2020, which claims the benefit of priority of U.S. Provisional Application No. 62/887,050 titled "DELIVERY PEPTIDES AND METHODS OF USING THE SAME" filed Aug. 15, 2019, the contents of which are incorporated herein by reference in their entirety.

REFERENCE TO AN ELECTRONIC SEQUENCE LISTING

The contents of the electronic sequence listing (NIBN-BGU-P-033-US_Corrected_ST25.txt; Size: 23,698 bytes; and Date of Creation: Nov. 4, 2025) is herein incorporated by reference in its entirety.

FIELD OF INVENTION

The present invention is in the field of delivery peptides.

BACKGROUND

Vitellogenin (Vg) is a major lipoprotein (LP) in oviparous animals being the precursor of the egg-yolk protein vitellin. It is essential for providing the metabolic demands of the developing embryo—and is one of the most abundant LPs in the hemolymph of reproductive (vitellogenic) females. In the giant prawn *Macrobrachium rosenbergii* which is widely cultured throughout the world (over 450,000 tons annually), vitellogenin (MrVg) is synthesized in the hepatopancreas, secreted to the hemolymph, and taken up by the ovary via receptor-mediated endocytosis (RME).

The RME mechanism involves a membrane-bound receptor that specifically binds a ligand molecule in the extracellular fluid. The ligand-receptor complex localized in regions of the plasma membrane termed "coated pits" and internalized via Clathrin-coated vesicles. Endocytosis events are pivotal in many different physiological processes with various types of ligands and receptors, and the basic mechanism appears to be conserved in all eukaryotes.

LPs and their membrane receptors are conserved throughout evolution, including the human ApoB, several low-density lipoproteins, and the crustacean Vg. The Vg receptor (VgR) belongs to the low-density LP receptor (LDLR) superfamily and contains several conserved domains, including the ligand-binding domains (LBDs), an epidermal growth factor (EGF)-like domain, an O-glycosylation domain, a transmembrane domain, and a short cytosolic tail. Studies of vertebrate and invertebrate LDLR and VgR found that the LBD is comprised of several repeats of about 40 amino acids. Each repeat contains six cysteine residues that form three disulfide bonds. It was found that these six cysteine repeats are important for the LDLR-LDL binding.

In a previous study, the crustacean *M. rosenbergii* VgR (MrVgR) was cloned and sequenced, and its putative protein was found to encompasses all of the above conserved domains, including LBD-I and LBD-II, which are characteristic of the arthropod VgRs. Furthermore, MrVgR was shown to specifically bind its ligand MrVg. In addition, a receptor blot assay of the *Xenopus laevis* vitellin, that is the ovarian-processed form of Vg, showed that the lipovitellin subunit which encompasses the lipid-binding domain interacts with the receptor. This latter finding is in line with previous work on vertebrate Vg which showed that the lipid-binding domain is necessary for the interaction with the VgR.

The most extensive study on Vg-VgR interaction was conducted in fish, the blue tilapia, *Oreochromis aureus*, where it was shown that VgR binds to the lipid binding domain at the N-terminal region of Vg. Accordingly, an 84 amino acid-long fragment from the N-terminal portion of *O. aureus* Vg was found to be sufficient for VgR binding.

There is still a great need for an agent capable of specifically delivering a cargo molecule, e.g., a dye, a polynucleotide, a protein, etc., to a cell, e.g., an oocyte.

SUMMARY

According to one aspect, there is provided a peptide consisting of 7 to 23 amino acids derived from the amino acid sequence: $DKX_1X_2X_2X_3PX_4X_5GX_6YKYVEAX_7X_8X_9SX_{10}X_{11}$ (SEQ ID NO: 1), wherein: $X_1$ is selected from the amino acid residues N and K; $X_2$ is selected from the amino acid residues I and V; $X_3$ is selected from the amino acid residues K and R; $X_4$ is selected from the amino acid residues A and S; $X_5$ is selected from the amino acid residues Y and I; $X_6$ is an amino acid residue selected from the group consisting of: S, I, A, and T; $X_7$ is an amino acid residue selected from the group consisting of: H, S, K and E; $X_8$ is selected from the amino acid residues Q and M; $X_9$ is an amino acid residue selected from the group consisting of: E, D, and M; $X_{10}$ is selected from the amino acid residues V and T; and $X_{11}$ is selected from the amino acid residues L and M.

According to another aspect, there is provided a chimera comprising: a first peptide, wherein the first peptide comprises the herein disclosed peptide; directly or indirectly bound to an agent selected from the group consisting of: a polynucleotide, a second peptide, a small molecule, or any combination thereof.

In some embodiments, the peptide comprises the amino acid sequence: $DKX_1X_2X_2X_3PX_4X_5GX_6YKYVEA$ (SEQ ID NO: 2), wherein: $X_1$ is selected from the amino acid residues N and K; $X_2$ is selected from the amino acid residues I and V; $X_3$ is selected from the amino acid residues K and R; $X_4$ is selected from the amino acid residues A and S; $X_5$ is selected from the amino acid residues Y and I; and $X_6$ is an amino acid residue selected from the group consisting of: S, I, A, and T.

In some embodiments, the peptide comprises the amino acid sequence: $DKX_1\ X_2X_2X_3PX_4$ (SEQ ID NO: 3), wherein: $X_1$ is selected from the amino acid residues N and K; $X_2$ is selected from the amino acid residues I and V; $X_3$ is selected from the amino acid residues K and R; and $X_4$ is selected from the amino acid residues A and S.

In some embodiments, the peptide comprises the amino acid sequence: $DKX_1\ X_2X_2X_3P$ (SEQ ID NO: 4), wherein: $X_1$ is selected from the amino acid residues N and K; $X_2$ is selected from the amino acid residues I and V; and $X_3$ is selected from the amino acid residues K and R.

In some embodiments, the peptide comprises the amino acid sequence: $GX_6YKYVEA$ (SEQ ID NO: 5), wherein $X_6$ is an amino acid residue selected from the group consisting of: S, I, A, and T.

In some embodiments, the agent is selected from the group consisting of: a polynucleotide, a second peptide, a small molecule, a dye, an embryo modifying agent, and any combination thereof.

In some embodiments, there is provided a polynucleotide encoding the herein disclosed peptide.

In some embodiments, there is provided an expression vector comprising the herein disclosed polynucleotide.

In some embodiments, there is provided a cell comprising any one of: (a) the herein disclosed peptide; (b) the chimera comprising the peptide; (c) the polynucleotide encoding the peptide; and (d) the expression vector comprising the polynucleotide.

In some embodiments, there is provided a composition comprising any one of: (a) the herein disclosed peptide; (b) the chimera comprising the peptide; (c) the polynucleotide encoding the peptide; (d) the expression vector comprising the polynucleotide; and (e) the cell comprising any one of: (a), (b), (c) and (d), and a carrier.

In some embodiments, the chimera is for use in the delivery of an agent into a cell.

In some embodiments, there is provided a method for making the herein disclosed chimera, comprising binding the herein disclosed peptide to an agent, wherein the agent is selected from the group consisting of: a polynucleotide, a second peptide, a small molecule, a dye, an embryo modifying agent, and any combination thereof.

In some embodiments, there is provided a method for delivering an agent into a cell comprising contacting the cell with the herein disclosed chimera, thereby delivering the agent into the cell.

In some embodiments, there is provided a method for modifying a cell comprising contacting the cell with the herein disclosed chimera, thereby modifying the cell.

In some embodiments, the cell is a cell of an oviparous animal.

In some embodiments, the cell is a cell of an arthropod.

In some embodiments, the arthropod is a crustacean.

In some embodiments, the crustacean is a decapod crustacean.

In some embodiments, the cell is an ovarian cell.

In some embodiments, the ovarian cell is an oocyte.

In some embodiments, contacting comprises any one of in vivo contacting, in vitro contacting, and ex vivo contacting.

In some embodiments, contacting is administering an effective amount of the herein disclosed chimera to an early vitellogenic female.

In some embodiments, administering is administering to the ovary, the hemolymph, or both.

In some embodiments, administering is at least once a week administering.

In some embodiments, the method further comprises a step of crossing the administered female with a male.

In some embodiments, there is provided a progeny obtained from a crossing performed according to the herein disclosed method.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 4I-4N are fluorescent micrographs of oocytes and gills taken from an early vitellogenic female injected simultaneously with a Vg-TAMRA peptide or a control-FITC peptide. Confocal images of the Hoechst-stained oocytes and the Vg-TAMRA (4I) and control-FITC (4J) peptides individually by their respective excitation wavelength, and an overlay image (4K). Both Vg-TAMRA and control-FITC peptides can be detected in the gills (4L and 4M, respectively) and in the overlay image (4N).

Figure 1:
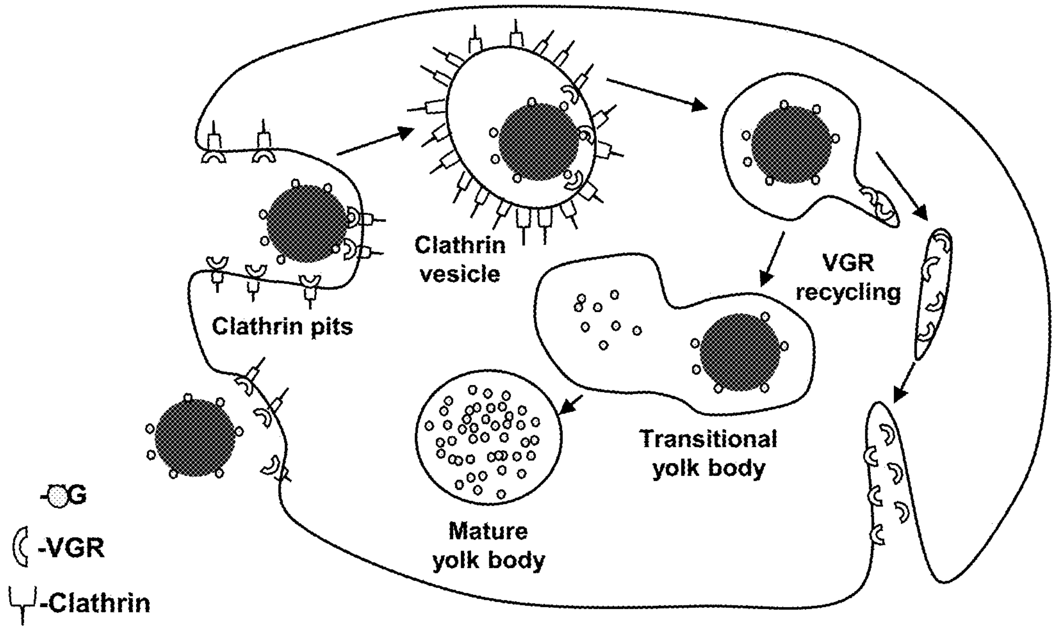
FIG. 1 includes a schematic illustration of receptor-mediated endocytosis of vitellogenin via Clathrin pits and receptor recycling.

(dsRNA kept at 25 μmol). Fluorescent images in 550 nm excitation (6C), and UV (6D) of an agarose gel loaded with a Lysine-Histidine tag (KH9) Vg conjugated with a 210 bp long dsRNA of PAX6 (Vg-dsPAX6). Constant amount (25 pmole) of dsPAX6 was conjugated with increasing amounts of Vg, thereby resulting in the following molar ratios: 1:1, 1:5, 1:10, 1:20, and 1:50, as indicated on each lane (6C-6D). Fluorescent images of ovary pieces incubated with Vg-dsPAX6 (6C), white arrowheads are directed toward orange puncta, which indicate overlapping of endocytosed dsPAX6-FITC and Vg-TAMRA (6E), white arrows indicate the scVg-dsPAX6 and dsPAX6 controls labelled with FITC are positioned on the outside of oocyte membrane (6F and 6G respectively).

FIGS. 7A-I to 7C include micrographs and graphs showing that Vg-dsRNA conjugates which was injected into reproductive females, imposed gene silencing, and retarded eye development in the embryos. FIGS. 7A-I to 7A-VI include images of embryos detached from a mother that was injected with Vg-dsPAX6 (7A-I to 7A-III) or from a mother that was injected with scVg-dsPAX6 (7A-IV to 7A-VI). Embryos possessing no or remnant eye development (7A-II, white arrowhead), cyclops embryo (7A-II, black arrowhead), or partially developed eyes (7A-III, gray arrowheads), were observed. (7B) includes a vertical bar graph showing the averaged length/width index of embryonic eyes of 9 days old embryos which were sampled from a mother that was injected with Vg-dsPAX6 (black column) or from a mother that was injected with scVg-dsPAX6 (gray column). (7C) includes a vertical bar graph showing the expression of epidermal growth factor receptor (EGFR) in larvae of either a mother which was injected with Vg-dsEGFR or of a control mother (i.e., injected with Vg-dsGFP, or with scVg-dsEGFR).

FIGS. 8A-I to 8C include micrographs and graphs showing that high dose injections into vitellogenesis-induced females leads to significant retarded eye development. (8A-I to 8A-VI) Embryos detached from a mother that was injected with Vg-dsPAX6 (8A-I to 8A-III) or a mother that was injected with dsPAX6 (8A-IV to 8VI). (8B) includes a vertical bar graph showing the averaged length/width index of embryo eyes taken from 10 days embryos of mother that were injected with Vg-dsPAX6 (dotted column) or dsPAX6 (striped column). (8C) includes a vertical bar graph showing the averaged length/width index of embryos eyes taken from the Vg-dsPAX6 injected females of the current (dotted column data from FIG. 9B) compared to the black column data from FIG. 7B.

FIGS. 9AI to 9C-III include micrographs showing that PAX6 silencing in embryos affects ommatids shape in advanced larvae stages. (9A-I to 9C-III) Scanning electron microscope (SEM) images of normal eye (9A-I to 9A-III) and irregular eye in larvae of treated females (9B-I to 9C-III). I, II, III represent different magnifications of ×500, ×1,000 and ×2,000, respectively.

FIGS. 10A-10E include an illustration, micrographs, multiple sequence alignments, and chromatograms showing that a Cas9-Vg active hybrid protein was cloned, expressed, purified, and administered. (10A) Scheme of the organization of a Cas9-Vg construct cloned into pET28B plasmid, and 3D structure prediction of the cloned fusion protein. (10B) UV illumination of sybersafe stained agarose gel showing the PAX6 DNA fragmentation in the presence of either commercial Cas9 or recombinant Cas9-Vg in the presence+or absence−of sgRNA. The assay had been performed with 600 ng recombinant or commercial Cas9. (10C) Coomassie-stained gel of the recombinant His-Cas9-Vg Ni-NTA elution fraction. (10D-10E) are multiple sequence alignments and chromatograms showing a case analysis and sequencing of DNA extracted from embryos that are the progeny of a mother that was administered with Cas9-Vg conjugated with PAX6 gRNA. (10D) Sanger chromatograms of the forward template (top) and the relative contribution of each sequence (bottom) depicting base deletion at the $3^{rd}$ or $4^{th}$ position upstream of PAM (CGG, dashed underline). (10E) Sanger chromatograms of the reverse template (top) and the relative contribution of each sequence (bottom), depicting base deletion at the 4th position downstream of PAM.

FIGS. 11A-11G include a chart and fluorescent micrographs showing that the VgR interacting region of Vitellogenin is highly conserved. (11A) A chart presenting a multiple sequence alignment of VgR interacting region of 26 amino acid obtained from *M. rosenbergii* and other six crustacean species. Filled areas depict identical amino acids among sequences. The row above each species sequence depicts the similarity to the *M. rosenbergii* sequence. Plus (+) sign indicates the exchange of an amino acid with another from the same characteristic group. (11B-11G) Fluorescent micrographs showing in vitro incubation of ovary pieces in the presence of Vg-derived peptide TAMRA and scVg-FITC simultaneously (Peptide sequences are disclosed in Table 4). (11B) Vg235-260, (11C) Vg237-244, (11D) Vg246-253, (11E) Vg237-253 (11F) Lv-Vg238-245, and (11G) Lv-Vg247-254.

DETAILED DESCRIPTION

The present invention is directed to a peptide capable of being internalized or endocytosed into an ovarian cell, e.g., an oocyte. In some embodiments, the peptide or fragment thereof is capable of delivering an agent into an ovarian cell.

In some embodiments, the peptide comprises or consists of 7 to 23 amino acids derived from the amino acid sequence: $DKX_1X_2X_2X_3PX_4X_5GX_6YKYVEAX_7X_8X_9SX_{10}X_{11}$ (SEQ ID NO: 1), wherein: $X_1$ is selected from the amino acid residues: N and K; $X_2$ is selected from the amino acid residues: I and V; $X_3$ is selected from the amino acid residues: K and R; $X_4$ is selected from the amino acid residues: A and S; $X_5$ is selected from the amino acid residues: Y and I; $X_6$ is an amino acid residue selected from: S, I, A and T; $X_7$ is an amino acid residue selected from: H, S, K and E; $X_8$ is selected from the amino acid residues: Q and M; $X_9$ is selected from the amino acid residues: E, D, and M; $X_{10}$ is selected from the amino acid residues: V and T; and $X_{11}$ is selected from the amino acid residues: L and M.

As used herein, the phrase “7 to 23 amino acids” comprises a peptide of at least 7, at least 8, at least 9, at least 10, at least 12, at least 15, at least 17, at least 19, at least 21, or at least 23 amino acids, or any value and range therebetween. Each possibility represents a separate embodiment of the invention. In some embodiments, 7 to 23 amino acids comprise 7 to 22, 8 to 20, 9 to 23, 10 to 17, 8 to 12, 9 to 19, 11 to 15, 10 to 13, 16 to 22, 17 to 19, 11 to 23, 14 to 19, 16 to 20, 9 to 16, or 8 to 11 amino acids. Each possibility represents a separate embodiment of the invention.

In some embodiments, the peptide comprises the amino acid sequence: $DKX_1X_2X_2X_3PX_4X_5GX_6YKYVEA$ (SEQ ID NO: 2), wherein: $X_1$ is selected from the amino acid residues: N and K; $X_2$ is selected from the amino acid residues: I and V; $X_3$ is selected from the amino acid residues: K and R; $X_4$ is selected from the amino acid residues: A and S; $X_5$ is selected from the amino acid residues: Y and I; and $X_6$ is an amino acid residue selected from: S, I, A and T.

In some embodiments, the peptide comprises the amino acid sequence: $DKX_1X_2X_2X_3PX_4$ (SEQ ID NO: 3), wherein: $X_1$ is selected from the amino acid residues: N and K; $X_2$ is selected from the amino acid residues: I and V; $X_3$ is selected from the amino acid residues: K and R; and $X_4$ is selected from the amino acid residues: A and S.

In some embodiments, the peptide comprises the amino acid sequence: $DKX_1X_2X_2X_3P$ (SEQ ID NO: 4), wherein: $X_1$ is selected from the amino acid residues: N and K; $X_2$ is selected from the amino acid residues: I and V; and $X_3$ is selected from the amino acid residues: K and R.

In some embodiments, the peptide comprises the amino acid sequence: $GX_6YKYVEA$ (SEQ ID NO: 5), wherein: $X_6$ is an amino acid residue selected from: S, I, A and T.

In one embodiment, the peptide comprises the amino acid sequence: DKNIIKPAYGSYKYVEA (SEQ ID NO: 6).

In one embodiment, the peptide comprises the amino acid sequence: DKNIIKP (SEQ ID NO: 7).

In one embodiment, the peptide comprises the amino acid sequence: DKNIVRPA (SEQ ID NO: 8).

In one embodiment, the peptide comprises the amino acid sequence: GSYKYVEA (SEQ ID NO: 9).

In one embodiment, the peptide comprises the amino acid sequence: GIYKYVEA (SEQ ID NO: 10).

In some embodiments, the peptide is further functionalized by the addition of a functional group to the peptide's N'-terminus, C'-terminus, or both. In some embodiments, the functional group is an amino acid. In some embodiments, the functional group is selected from a cysteine residue or a lysine residue.

The present invention encompasses derivatives of the peptide of the invention. The term "derivative" or "chemical derivative" includes any chemical derivative of the peptide having one or more residues chemically derivatized by reaction of side chains or functional groups, as long as the derivatized peptide maintains the herein disclosed peptide, i.e., Vg receptor (VgR) binding and subsequent induction of receptor-mediated endocytosis. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine (O) may be substituted for lysine.

In addition, a peptide derivative can differ from the natural sequence of the peptide of the invention by chemical modifications including, but are not limited to, terminal-$NH_2$ acylation, acetylation, methylation, phosphorylation, pegylation, or thioglycolic acid amidation, and by terminal-carboxlyamidation, e.g., with ammonia, methylamine, and the like. Peptides can be either linear, cyclic, or branched and the like, having any conformation, which can be achieved using methods known in the art, as long as the derivatized peptide is capable of binding to the VgR and subsequently induce receptor mediated endocytosis.

As used herein, the terms "peptide", "polypeptide" and "protein" are interchangeable, and refer to a polymer of amino acid residues, such as disclosed by SEQ ID NO: 1, or a fragment thereof comprising or consisting of 7-23 amino acids derived from SEQ ID NO: 1, for example SEQ ID Nos.: 2-10.

The term "amino acid" as used herein means an organic compound containing both a basic amino group and an acidic carboxyl group.

The term "amino acid residue" as used herein refers to the portion of an amino acid that is present in a peptide.

The term "peptide bond" means a covalent amide linkage formed by loss of a molecule of water between the carboxyl group of one ammo acid and the ammo group of a second ammo acid.

The terms "peptide", and "protein" as used herein encompass native peptides, peptidomimetics (typically including non-peptide bonds or other synthetic modifications) and the peptide analogs peptoids and semi-peptoids or any combination thereof. In another embodiment, the terms "peptide", and "protein" apply to amino acid polymers in which at least one amino acid residue is an artificial chemical analog of a corresponding naturally occurring amino acid.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to an aspartic acid (D).

As used herein, the phrase "conservative substitution" also includes the use of a chemically derivatized residue in place of a non-derivatized residue provided that such peptide displays the requisite function as specified herein.

Peptide derivatives can also include side chain bond modifications, including but not limited to $—CH_2—NH—$, $—CH_2—S—$, $—CH_2—S{=}O$, $OC—NH—$, $—CH_2—O—$, $—CH_2—CH_2—$, $S—C—NH—$, and $—CH{=}CH—$, and backbone modifications such as modified peptide bonds. Peptide bonds ($—CO—NH—$) within the peptide can be substituted, for example, by N-methylated bonds ($—N(CH_3)—CO—$); ester bonds ($—C(R)H—C—O—O—C(R)H—N$); ketomethylene bonds ($—CO—CH_2—$); a-aza bonds ($—NH—N(R)—CO—$), wherein R is any alkyl group, e.g., methyl; carba bonds ($—CH_2—NH—$); hydroxyethylene bonds ($—CH(OH)—CH_2—$); thioamide bonds ($—CS—NH$); olefmic double bonds ($—CH—CH—$); and peptide derivatives ($—N(R)—CH_2—CO—$), wherein R is the "normal" side chain, naturally presented on the carbon atom. These modifications can occur at one or more of the bonds along the peptide chain and even at several (e.g., 2-3) at the same time.

Peptide Synthesis

According to one embodiment, the peptide of the invention may be synthesized or prepared by any method and/or technique known in the art for peptide synthesis.

According to another embodiment, the peptide may be synthesized by a solid phase peptide synthesis method of Merrifield (see J. Am. Chem. Soc, 85:2149, 1964). According to another embodiment, the peptide of the invention can be synthesized using standard solution methods, which are well known in the art (see, for example, Bodanszky, M., Principles of Peptide Synthesis, Springer-Verlag, 1984).

In general, the synthesis methods comprise sequential addition of one or more amino acids or suitably protected amino acids to a growing peptide chain bound to a suitable resin. Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5 dimethoxybenzyloxycarbonyl, o-nitrophenylsulfenyl, 2-cyano-t-butyloxycarbonyl, 9-fluorenylmethyloxycarbonyl (Fmoc) and the like. In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic peptide synthesizer as is well known in the art.

In another embodiment, a peptide of the invention may be synthesized such that one or more of the bonds, which link the amino acid residues of the peptide are non-peptide bonds. In another embodiment, the non-peptide bonds include, but are not limited to, imino, ester, hydrazide, semicarbazide, and azo bonds, which can be formed by reactions well known to one skilled in the art.

The invention further encompasses a polynucleotide sequence comprising a nucleic acid encoding any of the peptides of the invention. In another embodiment, the nucleic acid sequence encoding the peptide is at least 70%, or alternatively at least 80%, or alternatively at least 90%, or alternatively at least 95%, or alternatively at least 99% homologous to the nucleic acid sequence encoding the nucleic acid sequence of the peptides of the invention or a derivative thereof, or any value and range therebetween. Each possibility represents a separate embodiment of the invention.

In some embodiment, the invention provides a polynucleotide encoding the peptide of the invention. In some embodiments, the invention provides a polynucleotide encoding the chimera of the invention.

In some embodiments, a polynucleotide molecule encodes a peptide comprising non-canonical amino acids.

In some embodiments, the polynucleotide of the invention is ligated into an expression vector, comprising a transcriptional control of a cis-regulatory sequence (e.g., promoter sequence). In some embodiments, the cis-regulatory sequence is suitable for directing constitutive expression of the peptide of the invention. In some embodiments, the cis-regulatory sequence is suitable for directing tissue-specific expression of the peptide of the invention. In some embodiments, the cis-regulatory sequence is suitable for directing inducible expression of the peptide of the invention.

The term "polynucleotide" refers to a nucleic acid (e.g., DNA or RNA) sequence that comprises coding sequences necessary for the production of a peptide. In one embodiment, a polynucleotide refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA-dependent DNA polymerase. In one embodiment, the sequence can be subsequently amplified in vivo or in vitro using a DNA polymerase.

In one embodiment, "genomic polynucleotide sequence" refers to a sequence derived or isolated from a chromosome and, thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the peptide of the invention, as well as some intronic sequences interposing therebetween. In one embodiment, the intronic sequences can be of any source, including of other genes, and typically may include conserved splicing signal sequences. In one embodiment, intronic sequences include cis-acting expression regulatory elements.

In some embodiments, a polynucleotide of the invention is prepared using PCR techniques, or any other method or procedure known to one of ordinary skill in the art.

In some embodiments, an expression vector comprising a polynucleotide encoding the peptide of the invention or a chimera comprising the same, is provided.

In one embodiment, a polynucleotide of the invention is inserted into expression vectors (i.e., a nucleic acid construct) to enable expression of a recombinant peptide. In one embodiment, the expression vector includes additional sequences which render this vector suitable for replication and integration in prokaryotes. In one embodiment, the expression vector includes additional sequences which render this vector suitable for replication and integration in eukaryotes. In one embodiment, the expression vector includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In some embodiments, a cell comprising any one of: the peptide of the invention; a chimera comprising the same; a polynucleotide encoding the peptide of the invention; and an expression vector comprising the polynucleotide encoding the peptide of the invention, is provided.

In one embodiment, a variety of prokaryotic or eukaryotic cells can be used as host-expression systems to express the peptide of the invention. In some embodiments, these include, but are not limited to, microorganisms, such as bacteria transformed with a recombinant bacteriophage DNA, plasmid DNA or cosmid DNA expression vector containing the peptide coding sequence; yeast transformed with recombinant yeast expression vectors containing the peptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the peptide coding sequence.

In some embodiments, non-bacterial expression systems are used (e.g. mammalian expression systems) to express the peptide of the invention. In one embodiment, the expression vector is used to express the polynucleotide of the invention in mammalian cells.

In some embodiments, in bacterial systems, a number of expression vectors can be advantageously selected depending upon the use intended for the peptide expressed. In one embodiment, large quantities of peptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the peptide. In one embodiment, vectors adaptable to such manipulation include, but are not limited to, the pET series of *E. coli* expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector may further include additional polynucleotide sequences that allow, for example, the translation of several proteins from a single mRNA such as an internal ribosome entry site (IRES).

In some embodiments, mammalian expression vectors include, but are not limited to, pcDNA3, pcDNA3.1 (±), pGL3, pZeoSV2 (±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses can be used. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression of the peptide of the invention. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, the viral vectors that are produced are unable to spread laterally. In one embodiment, this characteristic can be useful if the desired purpose is to introduce a specified gene into only a localized number of targeted cells.

Various methods can be used to introduce an expression vector into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a peptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the peptide), the expression construct can also include sequences engineered to optimize stability, production, purification, yield or activity of the expressed peptide.

In some embodiments, transformed cells are cultured under effective conditions, which allow for the expression of high amounts of a recombinant peptide. In some embodiments, effective culture conditions include, but are not limited to, effective media, bioreactor, temperature, pH, and oxygen conditions that permit protein production. In one embodiment, an effective medium refers to any medium in which a cell is cultured to produce a recombinant peptide of the present invention. In some embodiments, a medium typically includes an aqueous solution having assimilable carbon, nitrogen and phosphate sources, and appropriate salts, minerals, metals and other nutrients, such as vitamins.

In some embodiments, the cells can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant peptide of the invention either remains within the recombinant cell, secreted into the fermentation medium, secreted into a space between two cellular membranes, such as the periplasmic space in *E. coli*; or retained on the outer surface of a cell or viral membrane. In one embodiment, following a predetermined time in culture, recovery of the recombinant peptide is affected.

In one embodiment, the phrase "recovering the recombinant peptide" as used herein, refers to collecting the whole fermentation medium containing the peptide and need not imply additional steps of separation or purification.

In one embodiment, a peptide of the invention is purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the peptide of the invention and fused cleavable moiety. In one embodiment, a fusion protein can be designed so that the peptide can be readily isolated by affinity chromatography; e.g., by immobilization on a column specific for the cleavable moiety. In one embodiment, a cleavage site is engineered between the peptide and the cleavable moiety, and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the peptide of the invention is retrieved in "substantially pure" form that allows for the effective use of the protein in the applications described herein.

As used herein, the term "substantially pure" describes a peptide or other material which has been separated from its native contaminants. Typically, a monomeric peptide is substantially pure when at least about 60 to 75% of a sample exhibits a single peptide backbone. Minor variants or chemical modifications typically share the same peptide sequence. A substantially pure peptide can comprise over about 85 to 90% of a peptide sample, and can be over 95% pure, over 97% pure, or over about 99% pure, or any value and range therebetween. Each possibility represents a separate embodiment of the invention. Purity can be measured on a polyacrylamide gel, with homogeneity determined by staining. Alternatively, for certain purposes high resolution may be necessary and HPLC or a similar means for purification can be used. For most purposes, a simple chromatography column or polyacrylamide gel can be used to determine purity.

The term "purified" does not require the material to be present in a form exhibiting absolute purity, exclusive of the presence of other compounds. Rather, it is a relative definition. A peptide is in the "purified" state after purification of the starting material or of the natural material by at least one order of magnitude, 2 or 3, or 4 or 5 orders of magnitude.

In one embodiment, the peptide of the invention is substantially free of naturally associated host cell components. The term "substantially free of naturally-associated host cell components" describes a peptide or other material which is separated from the native contaminants which accompany it in its natural host cell state. Thus, a peptide which is chemically synthesized or synthesized in a cellular system different from the host cell from which it naturally originates will be free from its naturally associated host cell components.

In one embodiment, the peptide of the invention can also be synthesized using in vitro expression systems. In one embodiment, in vitro synthesis methods are well known in the art and the components of the system are commercially available. Non-limited example for in vitro system includes, but is not limited to in vitro translation, such as exemplified herein below.

Chimera

As used herein, the term "chimera" encompasses any conjugate comprising two or more moieties, wherein the two or more moieties are bound to one another either directly or indirectly, and wherein the moieties are either derived from distinct origins or are not naturally bound to one another. In some embodiments, the two or more moieties have: distinct functions, originate or derived from different genes, peptides, genomic regions, or species, distinct chemical classification (e.g., a peptide and a polynucleotide, as exemplified herein).

In some embodiments, the chimera of the invention comprises a first peptide, wherein the first peptide comprises the peptide of the invention bound directly or indirectly to an agent, wherein the agent is selected from: a nucleotide, an oligonucleotide, a polynucleotide, an amino acid, a peptide, a peptide, a protein, a small molecule, a synthetic molecule, an organic molecule, an inorganic molecule, a polymer, a synthetic polymer, or any combination thereof.

In some embodiments, the chimera of the invention comprises a first peptide comprising an amino acid sequence set forth in SEQ ID NO: 1. In some embodiments, the chimera of the invention comprises a first peptide comprising an amino acid sequence set forth in SEQ ID NO: 2. In some embodiments, the chimera of the invention comprises a first peptide comprising an amino acid sequence set forth in SEQ ID NO: 3. In some embodiments, the chimera of the invention comprises a first peptide comprising an amino acid sequence set forth in SEQ ID NO: 4. In some embodiments, the chimera of the invention comprises a first peptide comprising an amino acid sequence set forth in SEQ ID NO: 5.

In some embodiments, the chimera of the invention comprises a first peptide comprising an amino acid sequence set forth in any one of SEQ ID Nos.: 1-5, with the proviso of the full length vitellogenin protein. In some embodiments, the chimera of the invention comprises a first peptide comprising an amino acid sequence set forth in any one of SEQ ID Nos.: 1-5, wherein the first peptide is not the full length vitellogenin.

As used herein, the term "full length" refers to the native protein being the translation product of the vitellogenin encoding gene (e.g., from start codon, encoding Methionine to the stop codon). In some embodiments, the full length protein comprises native, linear, folded, un-folded, misfolded, denaturated, or any combination thereof, of a vitellogenin protein.

As used herein, the term "vitellogenin" refers to the precursor protein of the egg yolk protein (e.g., vitellin). In some embodiments, vitellogenin is an arthropod vitellogenin. In some embodiments, vitellogenin is a crustacean vitellogenin. In some embodiments, vitellogenin is the vitellogenin of a crustacean of the *Macrobrachium* genus. In some embodiments, vitellogenin is of a crustacean of the family of Penaeidae.

In some embodiments, the full length vitellogenin is the full length vitellogenin of *Macrobrachium rosenbergii* (Accession number BAB69831.1).

As used herein, the term "directly" refers to cases wherein the peptide of the invention is bound to the agent in a covalent bond.

As used herein, the term "indirectly" refers to cases wherein each of the peptide of the invention and the agent are bound to a linker or a spacing element and not directly to one another. In some embodiments, the peptide is covalently bound to the linker. In some embodiments, the agent is either covalently or non-covalently bound to the linker.

As used herein, the term "covalent bond" refers to any bond which comprises or involves electron sharing. Non-limiting examples of a covalent bond include, but are not limited to: peptide bond, glyosidic bond, ester bond, phosphor diester bond.

As used herein, the term "non-covalent bond" encompasses any bond or interaction between two or more moieties which do not comprise or do not involve electron sharing. Non-limiting examples of a non-covalent bond or interaction include, but are not limited to, electrostatic, x-effect, van der Waals force, hydrogen bonding, and hydrophobic effect.

The term "linker" refers to a molecule or macromolecule serving to connect different moieties of the chimera, that is the peptide of the invention and the agent. In one embodiment, a linker may also facilitate other functions, including, but not limited to, preserving biological activity, maintaining sub-units and domains interactions, and others.

In another embodiment, a linker may be a monomeric entity such as a single amino acid. In another embodiment, amino acids with small side chains are especially preferred, or a peptide chain, or polymeric entities of several amino acids. In another embodiment, a peptide linker is 2 to 30 amino acids long, 2 to 25 amino acids long, 4 to 23 amino acids long, 4 to 20 amino acids long, 5 to 22 amino acids long, or 2 to 28 amino acids long. Each possibility represents a separate embodiment of the invention. In another embodiment, a peptide linker is at least 6 amino acids long, at least 8 amino acids long, at least 10 amino acids long, at least 12 amino acids long, at least 15 amino acids long, at least 17 amino acids long, at least 20 amino acids long, at least 22 amino acids long, at least 25 amino acids long, at least 27 amino acids long, or at least 30 amino acids long, or any value and range therebetween. Each possibility represents a separate embodiment of the invention. In one embodiment, a linker may be a nucleic acid encoding a small peptide chain. In another embodiment, a linker encodes a peptide linker of 6 to 30 amino acids long, 6 to 25 amino acids long, 7 to 23 amino acids long, 8 to 20 amino acids long, 10 to 22 amino acids long, or 12 to 28 amino acids long. Each possibility represents a separate embodiment of the invention. In another embodiment, a linker encodes a peptide linker of at least 6 amino acids long, at least 8 amino acids long, at least 10 amino acids long, at least 12 amino acids long, at least 15 amino acids long, at least 17 amino acids long, at least 20 amino acids long, at least 22 amino acids long, at least 25 amino acids long, at least 27 amino acids long, or at least 30 amino acids long, or any value and range therebetween. Each possibility represents a separate embodiment of the invention.

In some embodiments, a peptide of the invention and a peptide linker are transcribed from a single polynucleotide sequence. In some embodiments, the peptide of the invention and a peptide linker are transcribed from a single polynucleotide sequence so as to provide the chimera of the invention. In some embodiments, the peptide of the invention and the peptide linker reside within a single peptide chain. In some embodiments, the peptide of the invention and the peptide linker are adjacent to one another in a manner that the last amino acid at the C' terminus of the peptide of the invention is bound via a peptide bond to the first amino acid of the N' terminus of the peptide linker. In some embodiments, the peptide of the invention and the peptide linker are adjacent to one another in a manner that the first amino acid at the N' terminus of the peptide of the invention is bound via a peptide bond to the last amino acid of the C' terminus of the peptide linker.

In some embodiments, the peptide of the invention may be attached or linked to an agent via a chemical linker. Chemical linkers are well known in the art and include, but are not limited to, dicyclohexylcarbodiimide (DCC), N-hydroxysuccinimide (NHS), maleiimidobenzoyl-N-hydroxysuccinimide ester (MBS), N-ethyloxycarbonyl-2-ethyloxy-1,2-dihydroquinoline (EEDQ), N-isobutyloxy-carbonyl-2-isobutyloxy-1,2-dihydroquinoline (IIDQ).

Recombinant technology may be used to express the peptide of the invention, and is well known in the art. In another embodiment, the linker may be a cleavable linker, resulting in cleavage of the peptide of the invention once delivered to the tissue or cell of choice. In such an embodiment, the cell or tissue would have endogenous (either naturally occurring enzyme or be recombinantly engineered to express the enzyme) or have exogenous (e.g., by injection, absorption, or the like) enzyme capable of cleaving the cleavable linker.

In another embodiment, the linker may be biodegradable such that the peptide of the invention is further processed by hydrolysis and/or enzymatic cleavage inside cells. In some embodiments, a readily cleavable group include acetyl, trimethylacetyl, butanoyl, methyl succinoyl, t-butyl succinoyl, ethoxycarbonyl, methoxycarbonyl, benzoyl, 3-amino-cyclohexylidenyl, and the like.

In some embodiments, a peptide linker has an electric charge at a pH ranging from 6.5 to 8.

In some embodiments, the linker has a positive electric charge. In some embodiments, the linker has a negative electric charge.

In one embodiment, a peptide linker comprises 2-30 amino acid residues selected from: lysine, arginine, histidine, aspartic acid, glutamic acid, and any combination thereof.

In one embodiment, a peptide linker comprises a polynucleotide binding region or domain, wherein the polynucleotide is selected from DNA, RNA, or a hybrid thereof.

In some embodiments, a chimera comprising a peptide linker and a polynucleotide agent comprises a peptide linker comprising 4 to 8, 4 to 12, 6 to 14, 8 to 16, 8 to 20, 10 to 24, 6 to 28, or 2 to 30 amino acids, or any value and range therebetween, and a polynucleotide agent comprising 200 to 500, 150 to 750, 250 to 650, 500 to 700, 450 to 550, 250 to 475, 350 to 650, or 200 to 700 base pairs, or any value and range therebetween. Each possibility represents a separate embodiment of the invention.

In some embodiments, the chimera comprises the polynucleotide agent and the peptide linker in a weight/weight ratio ranging from 1:1 (w/w) to 1:50 (w/w). In some embodiments, 1:1 (w/w) to 1:50 (w/w) comprises 1:1 (w/w)

to 1:2 (w/w), 1:1 (w/w) to 1:5 (w/w), 1:1 (w/w) to 1:15 (w/w), 1:1 (w/w) to 1:20 (w/w), 1:1 (w/w) to 1:25 (w/w), 1:1 (w/w) to 1:30 (w/w), 1:1 (w/w) to 1:35 (w/w), 1:1 (w/w) to 1:40 (w/w), or 1:1 (w/w) to 1:45 (w/w). Each possibility represents a separate embodiment of the invention.

In some embodiments, the chimera has a size of at most 50 nm, at most 75 nm, at most 100 nm, at most 150 nm, at most 200 nm, at most 250 nm, at most 350 nm, at most 450 nm, or at most 500 nm, or any value and range therebetween. Each possibility represents a separate embodiment of the invention. In some embodiments, the chimera has a size of 50 to 550 nm, 100 to 500 nm, 150 to 550 nm, 125 to 375 nm, 50 to 300 nm, 225 to 435 nm, 200 to 400 nm, 175 to 385 nm, 215 to 305 nm, or 250 to 325 nm. Each possibility represents a separate embodiment of the invention.

In one embodiment, chimera size is the diameter or the radius of the chimera. In one embodiment, the structure or shape of the chimera is correlative, equivalent, or represented as a particle, for example a round or a spherical particle. In one embodiment, chimera size represents an average size of a plurality of chimeras. In one embodiment, chimera size is the average diameter or the average radius of the plurality of chimeras. As used herein, the terms “chimera size” and “particle size” are interchangeable.

In some embodiments, the chimera comprises a peptide linker comprising the amino acid sequence KHKHKHKHKHKHKHKHKHKH (SEQ ID NO: 11). In some embodiments, the chimera comprises a peptide linker comprising the amino acid sequence KHKHKHKHKHKHKHKH (SEQ ID NO: 12). In some embodiments, the chimera comprises a peptide linker comprising the amino acid sequence KHKHKHKHKHKHKH (SEQ ID NO: 13). In some embodiments, the chimera comprises a peptide linker comprising the amino acid sequence KHKHKHKHKHKH (SEQ ID NO: 14). In some embodiments, the chimera comprises a peptide linker comprising the amino acid sequence KHKHKHKHKH (SEQ ID NO: 15). In some embodiments, the chimera comprises a peptide linker comprising the amino acid sequence KHKHKHKH (SEQ ID NO: 16). In some embodiments, the chimera comprises a peptide linker comprising the amino acid sequence KHKHKH (SEQ ID NO: 17). In some embodiments, the chimera comprises a peptide linker comprising the amino acid sequence KHKH (SEQ ID NO: 18). In some embodiments, the chimera comprises a peptide linker comprising the amino acid sequence KH. In some embodiments, the chimera comprises a peptide linker comprising the amino acid sequence KKKKKKKKK (SEQ ID NO: 19).

In some embodiments, the chimera comprises a peptide linker comprising the amino acid sequence PVSLLQELCMRRGISPKYDLLQIEGAVHEPTFVYRVTVGEFAANGSGQSKKKA KHAAAKAVLDIII (SEQ ID NO: 20).

In some embodiments, the agent is selected from: a polynucleotide, a peptide, and a small molecule.

As used herein, the terms “agent” or “an embryo modifying agent” encompass any compound capable of modifying the activity, functionality, survival, fitness, appearance, structure, development, behavior, or any combination thereof, of an embryo, a larva developed therefrom, or a post larva developed therefrom. In some embodiments, the agent in an endogenous or exogenous molecule or compound. As used herein, the term “endogenous” refers to the fact that a compound is naturally produced in or by the contacted cell. As used herein, the term “exogenous” refers to the fact that a compound is not naturally produced in or by the contacted cell. In some embodiments, an exogenous agent is produced synthetically. In some embodiments, an exogenous agent is derived or obtained from any source or species other than the source or species that the contacted cell is derived from.

In some embodiments, the agent is a dye. In one embodiment, a dye is a fluorophore. In one embodiment, a dye is a quantum dot, i.e., a semiconducting particle of a few nm in size, typically 5 to 50 nm, having optical and electronic properties.

In some embodiments, modifying comprises altering the DNA sequence of the genome. In some embodiments, altering the DNA sequence of the genome comprises introduction of: a point mutation, an insertion, a deletion, an inversion, recombination, nick, double strand break, or any combination. In some embodiments, altering the DNA sequence of the genome comprises introduction of exogenous DNA (i.e., a transgene). In some embodiments, modifying comprises altering a gene’s expression profile. In some embodiments, altering a gene’s expression profile is either at the mRNA level, the protein level, or both. In some embodiments, modifying is silencing (or knocking down) the expression of a gene. In some embodiments, modifying is overexpressing (or upregulating) the expression of a gene. In some embodiments, altered gene expression at the mRNA level comprises: induction of mRNA degradation, increased mRNA instability or reduced mRNA stability, reduced mRNA transcription rate, reduced mRNA levels, reduced mRNA-ribosome interaction or recognition, or any combination thereof. In some embodiments, altered gene expression at the protein level comprises: reduced protein levels, reduced protein translation rate, inhibited or blocked protein translation, or any combination thereof.

In some embodiments, an agent, that is a polynucleotide is selected from: a single strand RNA, antisense RNA, siRNA, dsRNA, shRNA, guide RNA, micro RNA (miRNA), and DNA. As used herein, DNA refers to any deoxyribonucleic acid polymer, for example, complementary DNA (cDNA), a digested cDNA or genomic DNA (gDNA), a plasmid DNA, and the like. In some embodiments, an agent is any RNA interference (RNAi) inducing polynucleotide.

An antisense sequence as described herein comprises any one of: antisense oligonucleotide, ribozyme, external guide sequence (EGS) oligonucleotide, siRNA compound, single- or double-stranded RNA interference (RNAi) compound such as siRNA compound, modified bases/locked nucleic acid (LNA), antagomir, peptide nucleic acid (PNAs), or any other oligomeric compound or oligonucleotide mimetic capable of hybridizing to at least a portion of the target nucleic acid, such as a gene or a transcript thereof, and modulate its function. In some embodiments, the antisense sequence comprises an antisense RNA, antisense DNA, chimeric antisense oligonucleotide, antisense oligonucleotide comprising modified linkages, micro interfering RNA (miRNA), and a short hairpin RNA (shRNA).

As used herein, the term “interfering RNA” refers to any double stranded or single stranded RNA sequence, capable—either directly or indirectly (i.e., upon conversion)—of inhibiting or down regulating gene expression by mediating RNA interference. Interfering RNA includes but is not limited to siRNA and shRNA. RNAi refers to the selective degradation of a sequence-compatible messenger RNA transcript.

As used herein, the term “shRNA” refers to an RNA molecule comprising an antisense region, a loop portion, and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family.

As used herein, the term siRNA refers to any small RNA molecule capable of inhibiting or down regulating gene expression by mediating RNA interference in a sequence specific manner. The small RNA can be, for example, about 18 to 21 nucleotides long.

As used herein, the term dsRNA refers to any double stranded RNA molecule capable of inhibiting or down regulating gene expression by mediating RNA interference in a sequence specific manner. The dsRNA can be, for example, about 50 to 1,000 nucleotides long, about 50 to 500 nucleotides long, about 150 to 750 nucleotides long, or about 100 to 500 nucleotides long, or any value and range therebetween. Each possibility represents a separate embodiment of the invention.

In some embodiments, the agent is a peptide. In some embodiment, an agent that is a peptide is an enzyme. In some embodiments, an agent that is a peptide is an apoptosis inducer. The term "apoptosis inducer" encompasses any molecule or compound capable of inducing, or promoting programmed cell death, or any molecule or compound involved in the process of programmed cell death.

As used herein, the term "enzyme" encompasses any peptide capable of specifically catalyzing a reaction, i.e., an enzymatic procedure. As used herein, "enzymatic procedure" is any procedure catalyzed or performed by an enzyme, to name a few, nucleic acid molecule(s) ligation, reverse transcription, amplification, digestion, dephosphorylation, and others. An outcome of an enzymatic procedure comprises a desired product and by-products.

In some embodiments, an agent that is an enzyme is a DNA binding protein. In some embodiments, a DNA the binding protein comprises clustered regularly interspaced short palindromic repeat associated protein 9 system (CRISPR/Cas9). In some embodiments, an agent according to the present invention comprises the Cas9 protein.

In some embodiments, Cas9 protein comprises the amino acid sequence:

```
                              (SEQ ID NO: 21)
MDKKYSIGLDIGTNSVGWAVITDEYKVPSKKFKVLG

NTDRHSIKKNLIGALLFDSGETAEATRLKRTARRR

YTRRKNRICYLQEIFSNEMAKVDDSFEHRLEESEL

VEEDKKHERHPIFGNIVDEVAYHEKYPTIYHLRKK

LVDSTDKADLRLIYLALAHMIKFRGHFLIEGDLNP

DNSDVDKLFIQLVQTYNQLFEENPINASGVDAKAI

LSARLSKSRRLENLIAQLPGEKKNGLFGNLIALSL

GLTPNFKSNFDLAEDAKLQLSKDTYDDDLDNLLAQ

IGDQYADLFLAAKNLSDAILLSDILRVNTEITKAP

LSASMIKRYDEHHQDLTLLKALVRQQLPEKYKEIF

FDQSKNGYAGYIDGGASQEEFYKFIKPILEKMDGT

EELLVKLNREDLLRKQRTFDNGSIPHQIHLGELHA

ILRRQEDFYPFLKDNREKIEKILTFRIPYYVGPLA

RGNSRFAWMTRKSEETITPWNFEEVVDKGASAQSF

IERMTNFDKNLPNEKVLPKHSLLYEYFTVYNELTK
```

-continued

```
VKYVTEGMRKPAFLSGEQKKAIVDLLEKTNRKVTV

KQLKEDYFKKIECEDSVEISGVEDRFNASLGTYHD

LLKIIKDKDFLDNEENEDILEDIVLTLTLFEDREM

IEERLKTYAHLFDDKVMKQLKRRRYTGWGRLSRKL

INGIRDKQSGKTILDFLKSDGEANRNFMQLIHDDS

LTFKEDIQKAQVSGQGDSLHEHIANLAGSPAIKKG

ILQTVKVVDELVKVMGRHKPENIVIEMARENQTTQ

KGQKNSRERMKRIEEGIKELGSQILKEHPVENTQL

QNEKLYLYYLQNGRDMYVDQELDINRLSDYDVDHI

VPQSFLKDDSIDNKVLTRSDKNRGKSDNVPSEEVV

KKMKNYWRQLLNAKLITQRKFDNLTKAERGGLSEL

DKAGFIKRQLVETRQITKHVAQILDSRMNTKYDEN

DKLIREVKVITLKSKLVSDFRKDFQFYKVREINNY

HHAHDAYLNAVVGTALIKKYPKLESEFVYGDYKVY

DVRKMIAKSEQEIGKATAKYFFYSNIMNFFKTEIT

LANGEIRKRPLIETNGETGEIVWDKGRDFATVRKV

LS1VIPQVNIVKKTEVQTGGFSKESILPKRNSDKL

IARKKDWDPKKYGGFDSPTVAYSVLVVAKVEKGKS

KKLKSVKELLGITIMERSSFEKNPIDFLEAKGYKE

VKKDLIIKLPKYSLFELENGRKRMLASAGELQKGN

ELALPSKYVNFLYLASHYEKLKGSPEDNEQKQLFV

EQHKHYLDEIIEQISEFSKRVILADANLDKVLSAY

NKHRDKPIREQAENIIHLFTLTNLGAPAAFKYFDT

TIDRKRYTSTKEVLDATLIHQSITGLYETRIDLSQ

LGGDGGSGPPKKKRKVYPYDVPDYAC.
```

According to some embodiments, an agent that is an enzyme, such as Cas9, unwinds the DNA duplex and searches for sequences matching the crRNA to cleave. Target recognition occurs upon detection of complementarity between a "protospacer" sequence in the target DNA and the remaining spacer sequence in the crRNA. Importantly, Cas9 cuts the DNA only if a correct protospacer-adjacent motif (PAM) is also present at the 3' end. According to certain embodiments, different protospacer-adjacent motif can be utilized. For example, the *S. pyogenes* system requires an NGG sequence, where N can be any nucleotide. *S. thermophilus* Type II systems require NGGNG (Horvath and Barrangou, 2010) and NNAGAAW (Deveau, Barrangou et al. 2008). Bioinformatic analyses have generated extensive databases of CRISPR loci in a variety of bacteria that may serve to identify additional useful PAMs and expand the set of CRISPR-targetable.

The term "single guide RNA" (sgRNA), is a 20 bp RNA molecule that can form a complex with Cas9 and serve as the DNA recognition module. sgRNA is typically designed as a synthetic fusion of the CRISPR RNA (crRNA) and the trans-activating crRNA.

In some embodiments, the chimera comprises the peptide of the invention, Cas9 protein, a TRACER (i.e., trans-activating crRNA), and a sgRNA.

In some embodiments, a chimera comprises a plurality of chimeras. As used herein, a plurality of chimeras comprises at least 2 chimeras, at least 3 chimeras, at least 4 chimeras, or at least 5 chimeras, or any range therebetween. Each possibility represents a separate embodiment of the invention. In some embodiments, a plurality of chimeras comprises 2 to 3, 2 to 4, 2 to 5, 3 to 4, 3 to 5, or 4 to 5 chimeras. Each possibility represents a separate embodiment of the invention.

In some embodiments, a plurality of chimeras comprises a first chimera comprising a fusion peptide comprising the peptide of the invention, Cas9 protein, and a second chimera comprising the peptide of the invention a TRACER and a sgRNA. In some embodiments, in a plurality of chimeras, at least one chimera comprises the TRACER. In some embodiments, in a plurality of chimeras, not more than one chimera comprises the TRACER.

One skilled in the art will appreciate that any Cas9 known in the art may be utilized in the chimeras and methods described herein. The Cas9 (e.g., SaCas9 as described below) can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publicly available tools available to help choose and/or design target sequences as well as lists of bioinformatically determined unique gRNAs for different genes in different species, including but not limited to the Target Finder, (e.g., E-CRISP), the RGEN Tools: Cas-OFFinder, the CasFinder: Flexible algorithm for identifying specific Cas9 targets in genomes and the CRISPR Optimal Target Finder.

According to some embodiments, the method of the invention utilizes a dead-Cas9 (dCas9). The term "dCas9" as used herein refers to a Cas9 nuclease-null variant that is altered or otherwise modified to inactivate the nuclease activity. Such alteration or modification includes altering one or more amino acids to inactivate the nuclease activity or the nuclease domain. Such modification includes removing the peptide sequence or peptide sequences exhibiting nuclease activity, i.e. the nuclease domain, such that the peptide sequence or peptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes peptide sequences modified to inactivate nuclease activity or removal of a peptide sequence or sequences to inactivate nuclease activity. The nuclease-null DNA binding protein retains the ability to bind to DNA even though the nuclease activity has been inactivated. Accordingly, the DNA binding protein includes the peptide sequence or sequences required for DNA binding but may lack the one or more or all of the nuclease sequences exhibiting nuclease activity. Accordingly, the DNA binding protein includes the peptide sequence or sequences required for DNA binding but may have one or more or all of the nuclease sequences exhibiting nuclease activity inactivated.

In some embodiments, complementarity of a polynucleotide, such as an antisense polynucleotide as disclosed herein, for example a sgRNA, or dsRNA to a target nucleotide, such as a gene or transcript thereof, is at least 75%, at least 85%, at least 90%, at least 95%, at least 97%, at least 99%, or 100% complementary, or any range and value therebetween. Each possibility represents a separate embodiment of the invention. In some embodiments, complementarity of a polynucleotide, such as an antisense polynucleotide as disclosed herein, for example sgRNA or dsRNA, to a target nucleotide, such as a gene or transcript thereof, is 70-85%, 80-90% 92-97%, 95-99%, or 97-100%. Each possibility represents a separate embodiment of the invention.

In some embodiments, the method comprises mixing: (a) the chimera of the invention comprising the peptide of the invention and a Cas9 protein, and (b) a guide RNA configured to hybridize with a gene of interest, and contacting a cell with an effective amount of the resulting mixture.

In some embodiments, the method comprises mixing: (a) the chimera of the invention comprising the peptide of the invention and a Cas9 protein, and (b) a guide RNA configured to hybridize with a gene of interest, and administering an effective amount of the resulting mixture to an early vitellogenic female.

In some embodiments, the method comprises co-administering an effective amount of any one of: (a) the chimera of the invention comprising the peptide of the invention and a Cas9 protein, and (b) a guide RNA configured to hybridize with a gene of interest, to an early vitellogenic female.

In embodiments, co-administering comprises simultaneously administering. In some embodiments, co-administering comprises administering each of the (a) the chimera of the invention comprising the peptide of the invention and a Cas9 protein, and (b) a guide RNA configured to hybridize with a gene of interest, not at the same time or injection event. In some embodiments, co-administering comprises administering the chimera of the invention comprising the peptide of the invention and a Cas9 protein, and the guide RNA configured to hybridize with a gene of interest at least 5 sec, at least 1 min, at least 3 min, at least 5 min, at least 7 min, at least 10 min, at least 20 min, at least 30 min, at least 1 hr, at least 6 hr, at least 12 hr, or at least 1 day apart, or any value and range therebetween. Each possibility represents a separate embodiment of the invention.

In some embodiments, co-administering comprises administering the chimera of the invention comprising the peptide of the invention and a Cas9 protein at least 5 sec, at least 1 min, at least 3 min, at least 5 min, at least 7 min, at least 10 min, at least 20 min, at least 30 min, at least 1 hr, at least 6 hr, at least 12 hr, or at least 1 day after administering the guide RNA configured to hybridize with a gene of interest, or vice versa, or any value and range therebetween. Each possibility represents a separate embodiment of the invention.

In some embodiments, the term "a gene of interest" refers to any gene, the editing of which is desired, e.g., a developmental gene, a gene affecting survival, or others.

In some embodiments, "configured to hybridize" means the guide RNA comprises a nucleic acid sequence at least partially complementing the nucleic acid sequence of the gene of interest, thereby is capable of at least partially hybridize thereto.

Composition

In some embodiments, a composition comprising any one of: the peptide of the invention; a chimera comprising the peptide the invention; a polynucleotide encoding the peptide of the invention; an expression vector comprising the polynucleotide; a host cell comprising any one of the aforementioned, and a carrier, is provided.

In some embodiments, a composition comprising two or more peptides derived from SEQ ID NO: 1, wherein the two or more peptide have 99% sequence identity at most, is provided. In some embodiments, the amino acid sequences of the at least two peptides partially overlap or do not overlap.

In some embodiments, the herein disclosed composition is for use in the delivery of an agent to a cell. In some embodiments, the herein disclosed composition is for use in modifying a cell.

Method

In some embodiments, a method for making the herein disclosed chimera, comprising a step of binding the peptide of the invention to an agent selected from the group consisting of: a polynucleotide, a second peptide, a small molecule, or any combination thereof, is provided. In some embodiments, the method for making the chimera comprises producing the peptide of the invention. In some embodiments, producing the peptide of the invention comprises the expression the peptide of the invention from a polynucleotide encoding the peptide or from an expression vector comprising the polynucleotide, wherein the expression is a living cell, in an artificial cell, or in a cell free system. In some embodiments, the protein is produced synthetically, for example by a solid-state methodology. In some embodiments, the binding of the peptide of the invention to the agent, so as to provide the chimera comprises binding by polymerization. The term "binding by polymerization" refers to cases wherein the agent is a peptide, and that the peptide of the invention and the agent are transcribed as a single peptide from a single encoding polynucleotide. In some embodiments, the binding of the peptide of the invention to the agent, so as to provide the chimera comprises binding by ligation. The term "binding by ligation" refers to cases wherein each of the peptide of the invention and the agent are first produced separately (i.e., provided) and then are ligated or bound to one another so as to provide the chimera. In some embodiments, the ligation can be performed enzymatically or chemically. In some embodiments, the ligation of the peptide of the invention and the agent is directly or indirectly, as disclosed hereinabove.

In some embodiments, a method for delivering an agent into a cell comprising contacting the cell with the herein disclosed chimera, is provided.

In some embodiments, a method for modifying a cell comprising contacting the cell with the herein disclosed chimera, is provided.

In some embodiments, the cell is a cell of an oviparous animal. As used herein, the term "oviparous" refers to any organism which lays eggs, wherein the majority of embryonic development takes place, rather than in the mother. Non-limiting examples of oviparous species include arthropods, mollusks, fish, amphibians, reptiles, birds, and monotremes. Non-limiting examples of arthropods include for example, crustaceans, insects, arachnoids, chelicerates, and others.

In some embodiments, the cell is a cell of an arthropod.

In some embodiments, the arthropod is a crustacean. In some embodiments, the crustacean is a decapod crustacean. Non-limiting examples of a decapod crustacean include, but are not limited to, a prawns, a shrimp, a lobster, a crab, and a crayfish.

In some embodiments, the cell is an ovarian cell. In some embodiments, the ovarian cell is an oocyte. In some embodiments, an oocyte is selected from: a primary oocyte, a secondary oocyte, a mature oocyte, a previtellogenic oocyte, a partially vitellogenic oocyte, and a vitellogenic oocyte. In some embodiments, the ovarian cell is a follicular cell. In some embodiments, the ovarian cell is an ovarian epithelial cell and a germinal epithelial cell. In some embodiments, the ovarian cell is an oocyte-nourishing cell.

According to the method of the invention, in some embodiments thereof, contacting a cell with the chimera of the invention comprises any one of in vivo contacting, in vitro contacting, or ex vivo contacting.

In some embodiments, the method comprises administering an effective amount of the chimera of the invention to a previtellogenic female.

In some embodiments, the method further comprises a step of determining a female is a previtellogenic female, thereby is suitable for administration as disclosed herein.

Methods for determining vitellogenic state or stage are common and would be apparent to one of ordinary skill in the art. A non-limiting example include, but is not limited to, quantification of the levels of the vitellogenin protein in the circulation using an immunological assay, for example, enzyme linked immunosorbent assay.

In some embodiments, administering is injecting. In some embodiments, administering is administering to the ovary. In some embodiments, administering is injecting. In some embodiments, administering is administering to the hemolymph. In some embodiments, administering is administering to the ovary and the hemolymph. In some embodiments, administering is at least once a week, at least twice a week, or at least three times a week, or any range therebetween. Each possibility represents a separate embodiment of the invention. In some embodiments, administering is once or twice a week, once to three times a week, or twice or three times a week. Each possibility represents a separate embodiment of the invention.

As used herein, the term "hemolymph" refers to the circulation system.

In some embodiments, the method further comprises a step of crossing the administered female with a male. In some embodiments, crossing comprises mating with a male. In some embodiments, crossing comprises in vitro inseminating or in vitro fertilization. Methods of in vitro insemination or in vitro fertilization are common and would be apparent to one of ordinary skill in the art. Non-limiting examples include, but are not limited to, sperm or spermatophore collection and incubation with spawned eggs or placement on a receptive female, respectively.

In some embodiments, a progeny obtained from a crossing performed according to the method of the invention, is provided.

As used herein, the terms "subject" or "individual" or "animal" or "patient" or "mammal," refers to any subject, particularly a mammalian subject, for whom therapy is desired, for example, a human.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms “a”, “an” and “at least one” are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term “about.” Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, “comprise”, “include” and “have” and conjugates thereof, are used to indicate that the object or objects of the verb are not necessarily a complete listing of components, elements or parts of the subject or subjects of the verb.

Other terms as used herein are meant to be defined by their well-known meanings in the art.

Unless specifically stated or obvious from context, as used herein, the term “or” is understood to be inclusive.

Throughout this specification and claims, the word “comprise” or variations such as “comprises” or “comprising,” indicate the inclusion of any recited integer or group of integers but not the exclusion of any other integer or group of integers.

As used herein, the term “consists essentially of”, or variations such as “consist essentially of” or “consisting essentially of” as used throughout the specification and claims, indicate the inclusion of any recited integer or group of integers, and the optional inclusion of any recited integer or group of integers that do not materially change the basic or novel properties of the specified method, structure or composition.

As used herein, the terms “comprises”, “comprising”, “containing”, “having” and the like can mean “includes”, “including”, and the like; “consisting essentially of or “consists essentially” likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments. In one embodiment, the terms “comprises”, “comprising”, “having” are/is interchangeable with “consisting”.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, “Molecular Cloning: A laboratory Manual” Sambrook et al., (1989); “Current Protocols in Molecular Biology” Volumes I-III Ausubel, R. M., ed. (1994); Ausubel et al., “Current Protocols in Molecular Biology”, John Wiley and Sons, Baltimore, Maryland (1989); Perbal, “A Practical Guide to Molecular Cloning”, John Wiley & Sons, New York (1988); Watson et al., “Recombinant DNA”, Scientific American Books, New York; Birren et al. (eds.) “Genome Analysis: A Laboratory Manual Series”, Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; “Cell Biology: A Laboratory Handbook”, Volumes I-III Cellis, J. E., ed. (1994); “Culture of Animal Cells-A Manual of Basic Technique” by Freshney, Wiley-Liss, N. Y. (1994), Third Edition; “Current Protocols in Immunology” Volumes I-III Coligan J. E., ed. (1994); Stites et al. (eds), “Basic and Clinical Immunology” (8th Edition), Appleton & Lange, Norwalk, CT (1994); Mishell and Shiigi (eds), “Strategies for Protein Purification and Characterization-A Laboratory Course Manual” CSHL Press (1996); all of which are incorporated by reference. Other general references are provided throughout this document.

Materials and Methods

Custom Peptides

CDKNIIKPAYGSYKYVEAHQESVLRK-TAMRA (Vg; SEQ ID NO: 22); CQAPVKLIAYDKNKYEHEYRISVSGK-TAMRA or FITC (scVg; SEQ ID NO: 23); KHKHKHKHKHKHKHKHKHKHCDKNIIKPAYGSYKYVEAHQESVLRK-TAMRA (KHVg; SEQ ID NO: 24) and KHKHKHKHKHKHKHKHKHKHCQAPVKLIAYDKNKYEHEYRISVSGK-FITC (KHscVg; SEQ ID NO: 25) were purchased from Peptron (Yuseong-gu, Daejeon, Republic of Korea). For the in vitro tissue incubation experiments, Schneider's drosophila medium, Fetal Bovine Serum (FBS), and a mixture of antibiotics-Penicillin, Streptomycin, and Amphotericin B (PSA), concentration: Penicillin G sodium salt: 10,000 units/mL, streptomycin Sulfate: 10 mg/mL, Amphotericin B: 25 μg/mL, were purchased from Biological Industries (Beit HaEmek, Israel). Insulin and UTP-FITC were purchased from Sigma-Aldrich (St. Louis, Missouri).

Animals

*Macrobrachium rosenbergii* females were collected from the Aquaculture Station of the Ministry of Agriculture at Dor, Israel and held at Ben-Gurion University facility (27° C., 12 h daylight, fed ad libitum). Females used for the in vivo experiment were kept in a tank (5 females per tank), each female was held in a separate cage. A fertile male was set free in the tank.

Oocytes Imaging

Ovary pieces from in-vitro or in-vivo experiments were washed with Schneider's drosophila medium without the peptides for 5 min. Then, the pieces were torn apart on a slide in one drop of the medium to better view the individual oocytes. The slides were inspected, and images were taken by a confocal microscope FV1000 (Olympus) at ×60 magnification. The excitation laser wavelength was 561 nm for the TAMRA labelled peptides and 488 nm for FITC labelled control peptides, and the emission was obtained at 490-530 nm and 540-640 nm, respectively.

Synthesis of Double Stranded RNA (dsRNA)

dsRNA of the green fluorescence protein (GFP), epidermal growth factor receptor (EGFR) and paired box protein 6 (PAX6) were synthesized in vitro. pGEM-T Easy plasmids containing the genes ORF sequences served as templates for dsRNA synthesis. The templates were amplified by PCR, primed by two gene-specific primers with a T7 promotor site at the 5' of one primer (T7P) (see primers and T7 promotor sequences for dsRNA synthesis in Table 1). Primer pairs were as follows: the sense strand was synthesized using primer T7P forward vs. reverse primer, while the antisense strand was synthesized by T7P reverse vs. forward primer. PCR amplicons were electrophoresed on a 1.3% agarose gel, visualized with SYBR Safe DNA Gel Stain (Invitrogen) and UV light and purified with a PCR purification Kit (Nucleo-Spin Gel and PCR Clean-up, Machery-Nagel). The TranscriptAid T7 High Yield Transcription Kit (Thermo Scientific, Lithuania) was used to generate a single stranded RNA according to the manufacturer's instructions. RNA molecules were purified by phenol-chloroform (1:1) and sodium-acetate and precipitated with ethanol. Sense and antisense strands were hybridized by incubation at 70° C. for 15 min, 65° C. for 15 min and at room temperature for 30 min. dsRNA quality was assessed on an agarose gel and diluted to 5 mg/ml. dsRNA was kept at −80° C. until used. FITC labeled GFP dsRNA (dsGFP) was synthesized as described above by incorporation of UTP-FITC (1:1 ratio between the UTP and the UTP-FITS) in the synthesis reaction. RNA molecules were purified by Rneasy Minelute clean up kit (QIAGEN), followed by hybridization and quality assessment, as described above.

TABLE 1

Primers for dsRNA synthesis and for real-time RT-PCR

| Gene and size | Orientation | Sequence (5'-3') | SEQ ID NO: |
|---|---|---|---|
| dsGFP (720) | F | ATGGTGAGCA AGGGCGAGGA | 26 |
| | R | TTACTTGTAC AGCTCGTCCA T | 27 |
| dsMr-EGFR (650) | F | GAAAGATAGT GGTGCCTGCG TTA | 28 |
| | R | CTTTTCCCCA GCAACCTTCA TTA | 29 |
| dsMr-PAX6A (230) | F | GACTGGCTGC AAAGATAGGC | 30 |
| | R | GCCTGCCATA GACCCATAAG | 31 |
| dsMr-PAX6B (198) | F | TGGGTCGAGA CCATTCTCAT | 32 |
| | R | AGAGAAGACC GGCTTGTGAA | 33 |
| T7 promotor | F | TAATACGACT CACTATAGGG | 34 |
| QMr-EGFR (64, probe #50) | F | GAAAGAAAAT ACGCTCACCT TG | 35 |
| | R | AGTCACCTCT TGGACGTTGC | 36 |

Peptide-dsRNA Conjugation

Constant amount of dsRNA (25 pmole) solution was mixed with an increasing amount of peptide solution in an Eppendorf vial (~1.5 mL). The total conjugation reaction volume was completed to 15 μl with DEPC treated DDW. The solutions were incubated at room temperature for 20 minutes. To evaluate peptide-dsRNA conjugation, a 1.3% agarose gel was prepared in TAE buffer. Conjugates were mixed with equal volume of loading buffer (50% glycerol and 0.5 M EDTA). Peptide-dsRNA conjugates were separated for 30 minutes at 120 V. Fluorescent emission of conjugates in gels were scanned by using a Typhoon FLA 9500 gel system (GE Healthcare®).

In Vitro Incubation of Ovary Pieces with Peptides and Peptide-dsRNA Conjugates

*M. rosenbergii* ovary pieces of 1-3 mm with oocytes diameter of ~150 μm (early vitellogenic ovaries) were incubated in a sterile 24-wells plate, 2 $cm^2$ growth area each well (Biofil®) in a biological hood. Each piece was incubated with 250 μl Schneider's drosophila culture medium with osmolality fixed to 420 mOsm/L and supplemented with FBS (10%), PSA (final concentration: Penicillin-100 units/mL, streptomycin-0.1 mg/mL, Amphotericin B-0.25 μg/mL and insulin 10 mg/ml insulin in 25 mM HEPES). The ovary pieces were incubated either with Vg-TAMRA or scVg-TAMRA or with both Vg-TAMRA and scVg-FITC simultaneously (6 μM each). The plate was incubated at room temperature for 24 and 48 hours. To test dsRNA piggybacking, 55 pmole dsRNA was conjugated to 275 pmole either Vg-TAMRA or scVg-FITC peptides. Ovary pieces were incubated with the dsGFP-Vg-TAMRA or dsGFP-scVg-FITC conjugates and cultured as stated above.

In Vivo Assay—Peptide or Peptide-dsRNA Injection to Vitellogenic Females

Figure 2:
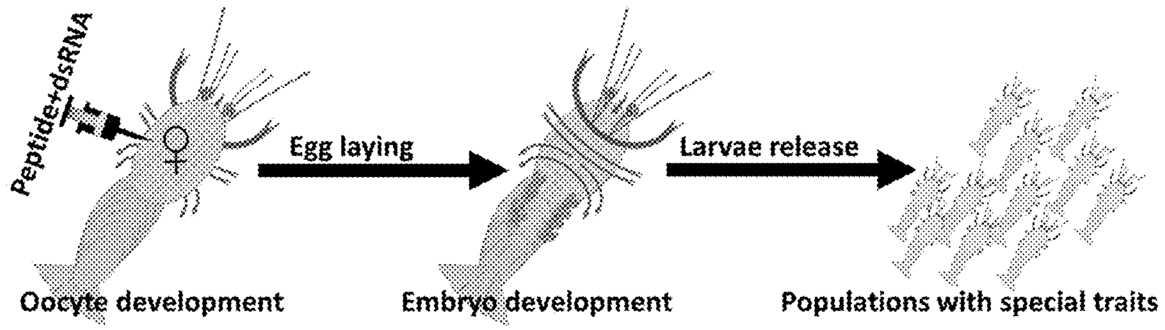
FIG. 2 includes a schematic non-limiting representation of the herein disclosed procedure.

Solution containing the culture medium, Vg-TAMRA and scVg-FITC peptides were injected (5 μg/gr body weight) into the hemolymph sinus at the base of the fifth walking leg of a *M. rosenbergii* reproductive females (14.3±0.4 gr, with opaque white to yellowish ovary, FIG. 2, left). For the injection, a manual micro dispenser syringe was used (Drummond®). After injection, the animals were kept at 28° C. for 24 hours in the culture facility for freshwater prawn *M. rosenbergii*, at Ben-Gurion University. Vg-dsEGFR or Vg-dsPAX6 conjugates (5:1 molar ratio for conjugation, 5 μg dsRNA/g body weight) were injected twice a week at the first two weeks. From the third week, the injections were performed once a week. The females were monitored daily and upon appearance of the reproductive molt, the females were released to a tank with a male for fertilization. The embryos' development on the pleopods of their mother (FIG. 2, middle) were monitored under stereoscope, and a fraction was collected for RNA extraction and subsequent quantitative PCR analysis.

Effects on Embryonic Eye Development

Figure 3:
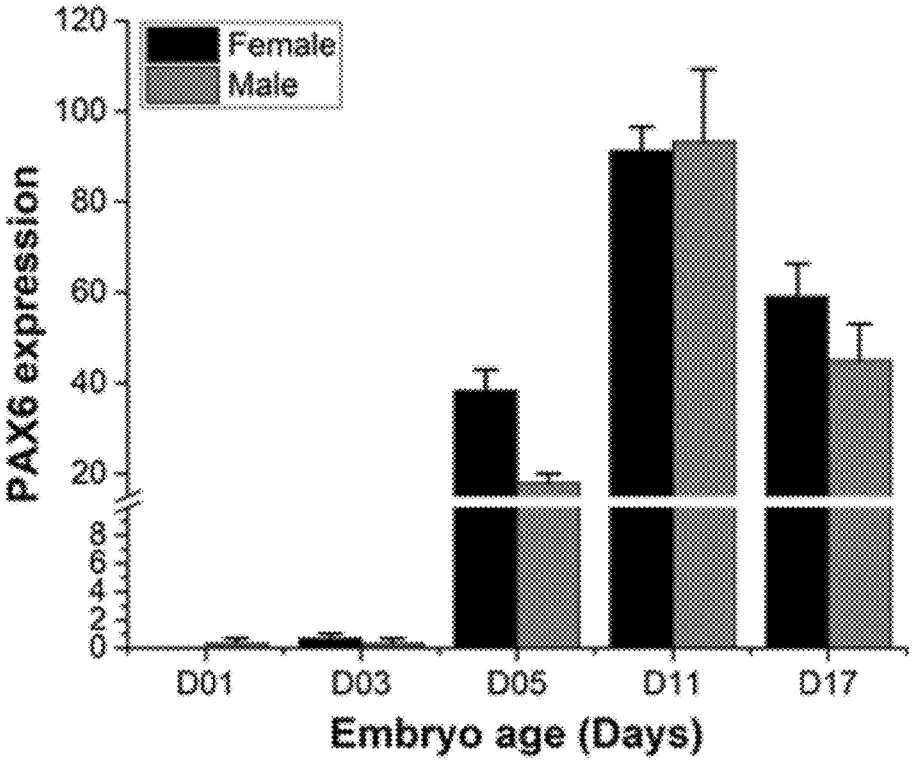
FIG. 3 includes a vertical bar graph showing the chronological paired box protein 6 gene (PAX6) expression during development of *M. rosenbergii* female and male embryos.

To in vivo evaluate the capability of piggybacking a functional dsRNA into the developing embryos (FIG. 2), the Vg-dsPAX6 conjugate was injected into *M. rosenbergii* reproductive females. PAX6 of *M. rosenbergii* homolog to an insect eye development gene and was found by us in an embryonic transcriptomic library to be expressed during mid-late embryonic development in both males and females (FIG. 3). To document the effect of PAX6 silencing on embryonic eye development, a sample of eggs containing embryos was collected from an egg-berried female on day 9 and monitored under a stereoscope. Embryos were counted and categorized to embryos with normal eyes, embryos with retarded eyes, and embryos with remnant or no eye development. Additionally, the dimensions (length and width) of the eye pigment were measured and an eye length/width index was calculated. The length/width index of ten pigmented eyes was measured under a microscope, in both eyes of the experimental group and of the control group.

Quantitative PCR Analysis

RNA was extracted from 9 days old embryos. Total RNA was isolated with the TRI RNA isolation reagent (Sigma-Aldrich, Israel), according to the manufacturer's instructions. First-strand cDNA was synthesized in a reverse-transcriptase reaction using a qScript cDNA synthesis kit (Quanta Biosciences, Gaithersburg, MD, USA) with 1 μg of total RNA according to the manufacturer's instructions.

Relative quantification of Mr-EGFR transcript levels was achieved using SensiFAST Probe Hi-ROX Mix (BIOLINE), specific primers, and a Universal ProbeLibrary (Roche) (see Table 1). Mr-18S rRNA (GenBank accession number GQ131934), serving as a normalizing gene, was also quantified by means of real-time RT-PCR using specific primers (see Table 1) with the above-mentioned mix and the Universal ProbeLibrary Probe 152 (Roche). Reactions were performed using the ABI Prism 7300 sequence detection system (Applied Biosystems, Foster City, California).

Example 1

Vg Peptide is Capable to Endocytose into Oocytes

Figure 4A:
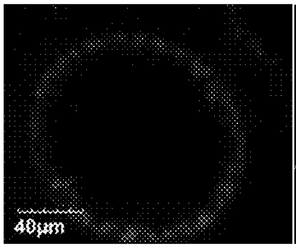
FIGS. 4A-4N include micrographs showing that the vitellogenin (Vg) peptide endocytosis into *M. rosenbergii* early vitellogenic oocytes. (4A) TAMRA fluorescent emission image; (4B) overlay of (4A) with the bright field image of oocyte incubated with the TAMRA fluorophore-labeled Vg peptide. (4C) TAMRA fluorescent emission; (4D) overlay of (4C) with the bright field image of oocyte incubated with the TAMRA fluorophore-labeled scrambled (sc) Vg peptide. The white arrow points toward the oocyte membrane and the black arrow points toward Vg accumulation inside the oocyte (4B). 4E-4H are images of oocytes from ovary pieces simultaneously incubated with Vg-TAMRA (red) and control-FITC (green) peptides. (4E) and (4F) are confocal images of the Vg-TAMRA and Control-FITC emission, respectively. (4G) Nuclear DNA of follicular cells staining with Hoechst (blue). (4H) is an overlay image of FIGS. 4E-4G.
Figure 4C:
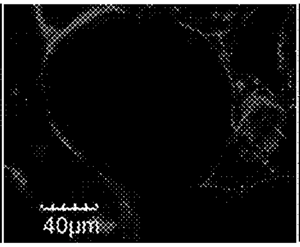
Figure 4E:
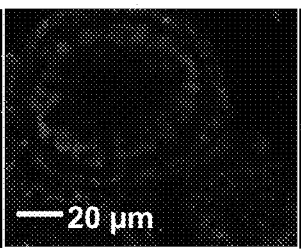
Figure 4G:
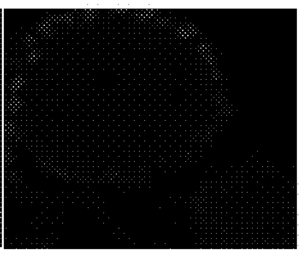
Figure 4B:
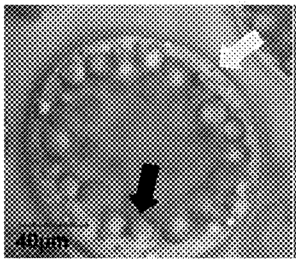
Figure 4D:
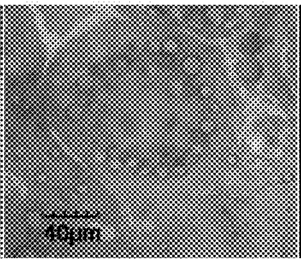
Figure 4F:
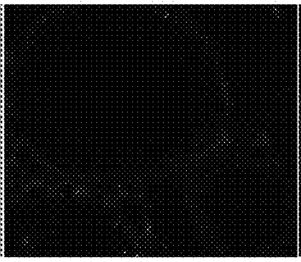
Figure 4H:
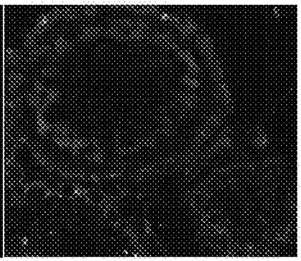
Figure 4I:
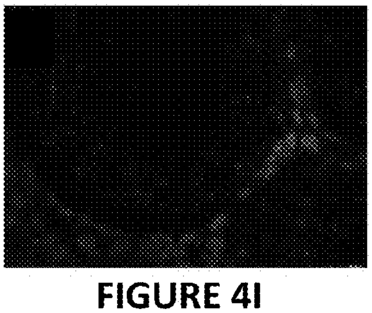
FIGS. 4I-4L are fluorescent images of oocytes and gills taken from an early vitellogenic female injected simultaneously with Vg-TAMRA and control-FITC peptides.
Figure 4J:
Figure 4K:
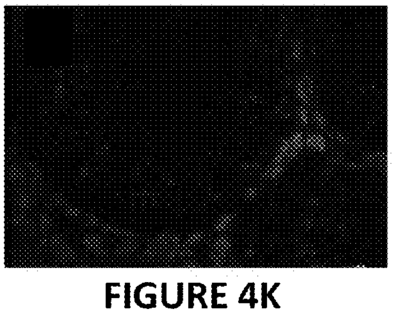
Figure 4L:
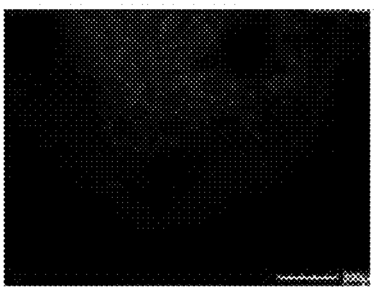
Figure 4M:
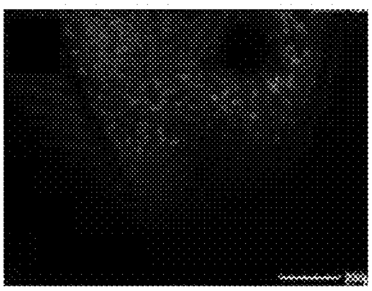
Figure 4N:
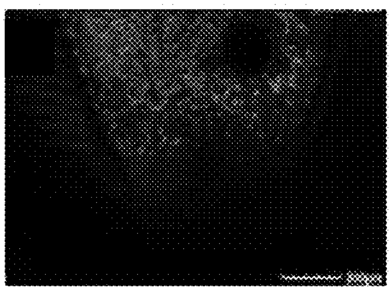
Figure 5A:
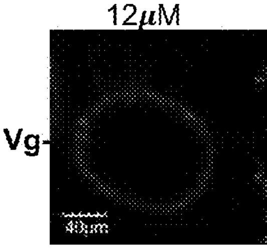
FIGS. 5A-5P include micrographs showing that the Vg peptide accumulates in the oocyte is a dose dependent manner. Ovary pieces incubated with gradual reduced concentrations of Vg or scVg peptides: 12 μM (5A, 5E, 5I, and 5M), 6 μM (5B, 5F, 5J, and 5N), 1.5 μM (5C, 5G, 5K, and 5O), and 0.75 μM (5D, 5H, 5L, and 5P). Oocytes incubated with Vg-TAMRA peptide are shown in fluorescent micrographs (5A-5D) and overlay with the bright field (5E-5H). Oocytes incubated with scVg-TAMRA peptide are shown in fluorescent micrographs (5I-5L) and overlay with the bright field (5M-5P).
Figure 5B:
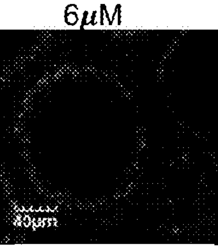
Figure 5C:
Figure 5D:
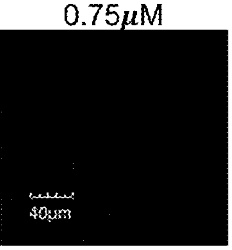
Figure 5E:
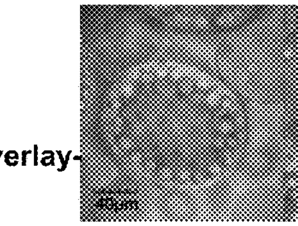
Figure 5F:
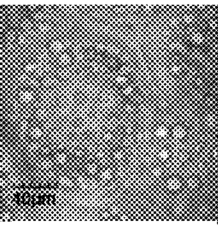
Figure 5G:
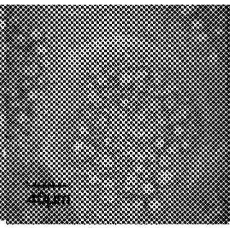
Figure 5H:
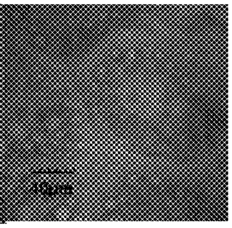
Figure 5I:
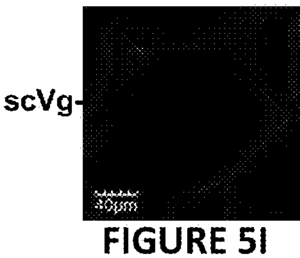
Figure 5J:
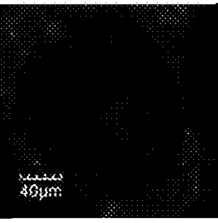
Figure 5K:
Figure 5L:
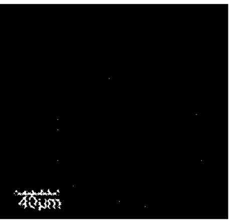
Figure 5M:
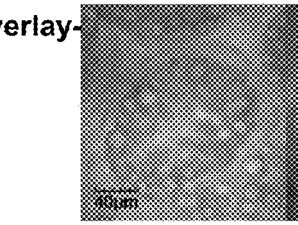
Figure 5N:
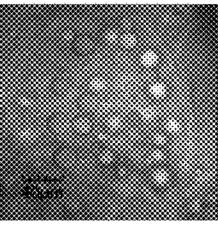
Figure 5O:
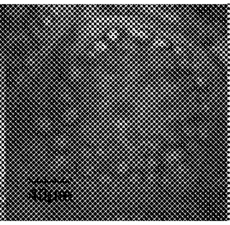
Figure 5P:
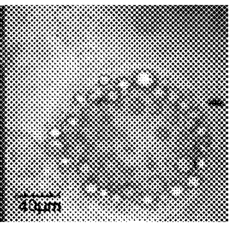

To evaluate the endocytosis capability of oocytes with respect to the newly designed Vg-derived peptides, an in vitro experiment was performed. Vg-derived and control peptides, labeled with TAMRA fluorophore, were detected by confocal microscopy. Both peptides were detected in the vicinity of the oocyte membrane (FIG. 4). Unlike the control peptide, the Vg peptide was distributed mainly at the cytosolic side of the oocyte membrane where yolk droplets are being formed (FIGS. 4A and 4B, black arrow) and was mostly accumulated at the peripheral area of the oocyte, near the membrane (FIG. 4B, white arrow) scattered on the external surface of newly formed droplets. Contrary to the above, the control peptide was mainly dispersed on the outer surface of the oocyte (FIGS. 4C and 4D). In order to get the highest certainty regarding the internalization specificity of the Vg-derived peptides, the Vg and control peptides were labelled with an additional fluorophore (FIGS. 4E-4H), Vg peptide was labelled with TAMRA (FIGS. 4E and 4H), while the control peptide has been labelled with FITC molecule (FIG. 4F). A similar result was obtained in this experiment showing distinct distribution of the two fluorescent-labelled peptides. Endocytosis of the Vg-TAMRA peptide into the oocytes was clearly observed, scattered along the inner side of the membranes. On the contrary, the control-FITC peptide could be seen only on the outer surface of the membrane (FIG. 4F).

To determine whether the Vg-TAMRA peptide has the capability to specifically in vivo internalize into oocytes, a mixture of the Vg-TAMRA and the control-FITC peptides were injected into the prawn circulatory system. The control-FITC peptide, 515 nm emission wavelength, was absent from oocytes dissected out 24 h after injection (FIG. 41). As for the Vg-TAMRA peptide, a clear 564 nm emission was seen inside the oocytes (FIGS. 4J and 4K), mostly inside yolk droplets. To verify that the two peptides did circulate through the prawn female body, the prawn gills were dissected and examined under the confocal microscope. A clear dual (TAMRA and FITC) emissions was observed (FIG. 4L), indicating that the majority of the injected peptides were washed away through the osmoregulatory system (i.e., the gills).

Example 2

The Vg Peptide Endocytose into the Oocytes in a Dose-Response Manner

Further, a dose dependent test with respect to Vg-derived peptides penetration into oocytes using Vg descending concentrations was performed (FIG. 5). Unlike the control scrambled peptide (scVg), the Vg peptide maintained similar pattern of distribution in the oocyte throughout the descending concentrations (FIG. 5, upper row). Another distinction between the Vg and control peptide, was noted in the fluorescence intensity. In both the fluorescence and overlay images, the Vg peptide presented a higher intensity of the red TAMRA emission (FIG. 5, two upper rows) in comparison to the control peptide images (FIG. 5, two lower rows). For Vg, a clear fluorescent signal was detected in concentration of 12 μM, 6 μM, and 1.5 μM, while the fluorescent signal of the control peptide was detected on the oocyte surrounding only as a weak fluorescent signal in high concentrations (12 μM and 6 μM) and no apparent signal detected in 1.5 μM. No signal was detected in 0.75 μM with both peptides (FIG. 5).

Example 3

Peptide-dsRNA Conjugate Internalization into Oocytes

Figure 6A:
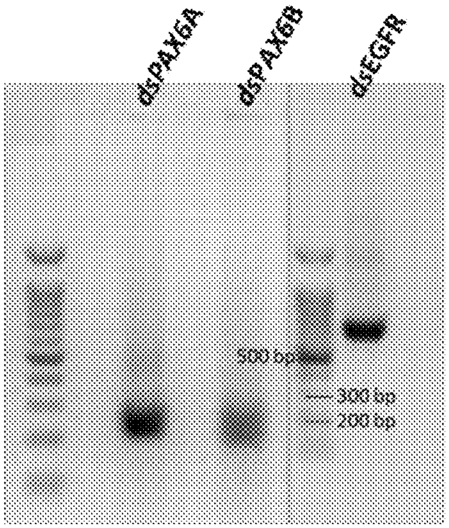
FIGS. 6A-6G include micrographs and a graph showing that the Vg-TAMRA peptide (Vg) is capable of piggybacking the conjugated dsRNA-FITC into oocytes, in vitro. (6A) A UV image of agarose gel separated double stranded (ds) RNA of dsPAX6A (198 bp), dsPAX6B (230 bp) and ds of epidermal growth factor receptor (dsEGFR), (700 bp). (6B) A graph of DLS measurements of dsRNA-peptide conjugates particle radius at molar ratios ranging from 1:1 to 1:30
Figure 6B:
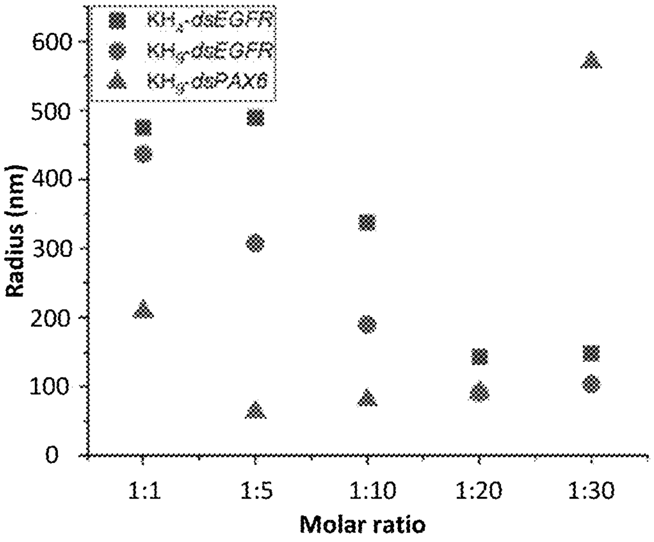

In order to verify whether the Vg-derived peptide was capable to piggyback and internalize a large molecule such as a dsRNA into the oocytes, a conjugation approach between the peptide and dsRNA was developed. The Vg-TAMRA and the control-FITC peptides were synthesized with a cationic poly lysine-histidine tail (KH) to allow electrostatic interactions between the peptides and the negatively charged dsRNA. The dsRNA-peptide complexes prepared at different molar ratios (peptide/dsRNA ratio: 1, 5, 10, 20 and 30) were characterized with two different assays: dynamic light scattering (DLS) and separation on agarose gel.

dsRNA of 700 bp (dsEGFR) and another one a mix of 200 and 230 bp dsRNA (dsPAX6) were prepared (FIG. 3A). The dynamic light scattering was done by conjugation of both peptides KH4-Vg and KH9-Vg with dsEGFR, while dsPAX6 was conjugated with KH9-Vg only. The DLS results indicate that conjugating the 700 bp dsRNA at a 1:1 ratio with either KH4-Vg or KH9-Vg leads to the formation of almost similar size particles (400-500 μm, FIG. 6B, squares and dots). However, at a higher peptide ratio, 1:30, the particles became smaller and the radius was reduced to ~100 nm (FIG. 6B dots). When KH9-Vg was mixed with the short dsRNA form (dsPAX6) the particle radius was smaller than 100 μm at a dsPAX6: peptide ratio of 1:5 (FIG. 6B, triangles).

Figure 6C:
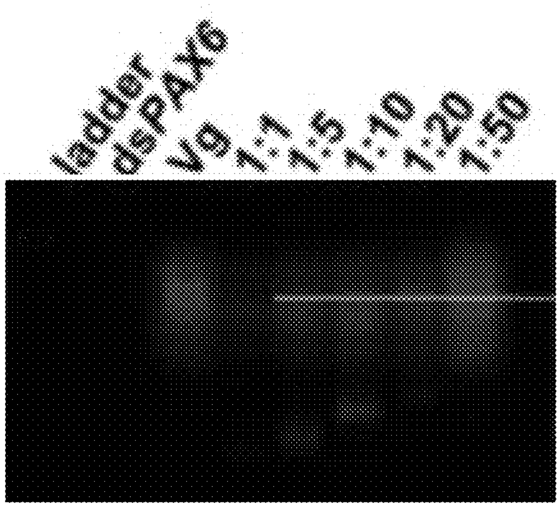
Figure 6D:
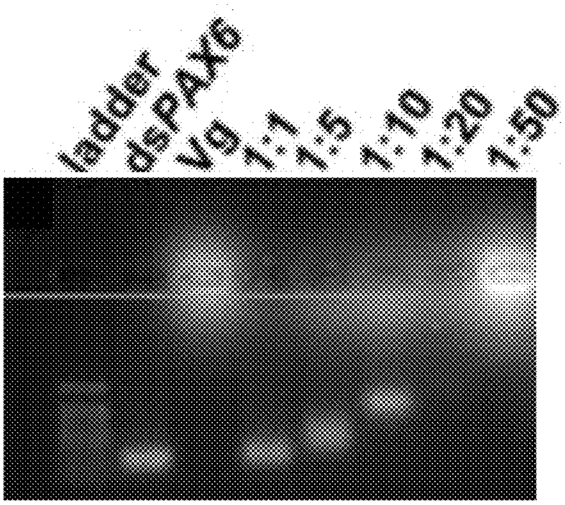
Figure 6E:
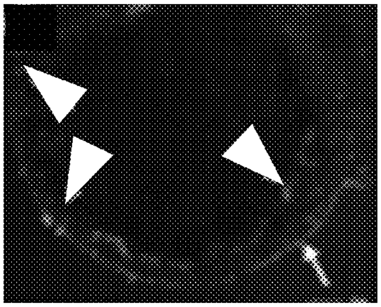
Figure 6F:
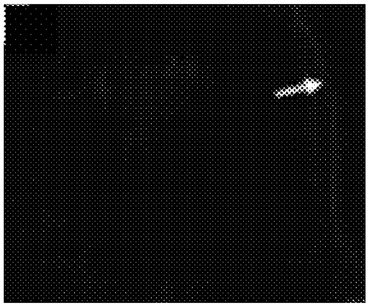
Figure 6G:
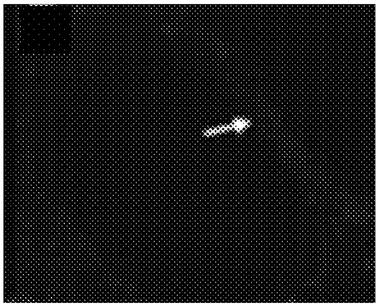

A constant dsRNA amount (25 pmole) obtained for the PAX6 gene (dsPAX6), was mixed with an increasing amount of the peptides. A gradual conjugate retardation in accordance with the peptides increasing amount was present in the agarose gel (FIGS. 6C-6D). The migration of the cationic peptides alone towards the cathode, was clearly observable in the gel fluorescent image (FIG. 6C). At ratios of 1:50 dsPAX6: peptide, excess free peptides or large aggregates that were retarded on or near the loading well, were clearly observed (FIG. 6C-6D). However, at a ratio of 1:5 a fluorescent signal could barely be seen on or near the loading well. Thus, to avoid any competition between conjugated and free peptide and to maximize the endocytosis of the conjugates to the oocytes, the 1:5 ratio of dsPAX6: peptide was selected for subsequent in-vitro and in-vivo experiments. The dsPAX6-peptide conjugate at a ratio of 1:5 was incubated in vitro with ovary pieces. Orange fluorescent puncta could be seen on the confocal image of oocytes incubated with the dsPAX6-Vg (FIG. 6E, yellow arrows), indicating that the green fluorescence of dsPAX6-FITC conjugated to the red fluorescent Vg-TAMRA are capable of oocyte internalization. Internalization of dsPAX6-FITC was concomitant with the internalization of the Vg-TAMRA (FIG. 6E). However, no green fluorescence puncta could be seen in the oocytes from ovary pieces that were incubated with dsPAX6 conjugated to the control peptide (FIG. 6F) or in the ovary pieces incubated with dsPAX6 alone (FIG. 6G).

Example 4

Silencing Capability of dsRNA-Peptide Conjugates in Embryos

Upon spawning and at the 9$^{th}$ day of development, fractions of incubated eggs (FIG. 2, middle) were sampled and the embryonic eye development was documented. Almost fifth of the embryo population taken from Vg-dsPAX6 injected females showed either diminished or lack of eye development (FIGS. 7A-I, 7A-II and 7A-III). A thin eye pigment line was abundant among those possessing diminished eye embryos (FIG. 7A-III, gray arrowheads). Single eyed embryos (cyclops) were also observed (FIG. 7A-II, black arrowhead). A complete lack of eye development or remnants of pigments were also observed (FIG. 7A-II, white arrowhead). The average of length/width index of the eye pigment was found to be significantly higher in embryos taken from the Vg-dsPAX6 treated female compared to embryos taken from scVg-dsPAX6 treated females (FIG. 7B).

Example 5

Silencing Capability of dsRNA-Peptide Conjugates in Larvae

When Vg conjugated to EGFR dsRNA (dsEGFR) and injected into vitellogenic females, the larvae of such female (FIG. 2, left) ~21 days post spawning, expressed significantly lower level of EGFR compared to the larvae of females that were injected with dsEGFR-control peptide or dsEGFR alone (FIG. 7C). It is noteworthy that for the dsEGFR quantitative PCR, the mRNA was collected from larvae. These larvae hatched from eggs that were laid 21 days earlier and that the mother received a dsEGFR-peptide conjugate few days before laying. This means, that the injected dsEGFR was still present and effectively induced gene silencing in the progeny more than three weeks after last injection.

Example 6

Optimization of dsRNA: Peptide Particle Size

The inventors examined the effect of dsRNA size (i.e., length), linker tail length, and dsRNA: Peptide ratio on particle size. The linker used comprised Lysine-Histidine repeats (KH). Dynamic light scattering (DLS) was used for determining the resulting particle's size (represented as particle's radius in nm). The results are shown herein below (Tables 2-3).

TABLE 2

Particle size of dsRNA:(KH)9-Vg peptide, as measured by DLS

| dsRNA length | Particle radius (nm): dsRNA only | dsRNA to (KH)9-Vg peptide 1:1 | 1:5 | 1:10 | 1:20 | 1:30 | 1:50 |
|---|---|---|---|---|---|---|---|
| 700 bp | 492.4 | 437 | 308 | 190 | 91.64 | 104.6 | 68.45 |
| 210 bp | 365 | 209 | 64 | 42.5 | 92.5 | 576 | — |

TABLE 3

Particle size of dsRNA:(KH)4-Vg peptide, as measured by DLS

| dsRNA length | Particle radius (nm): dsRNA only | dsRNA to (KH)4-Vg peptide 1:1 | 1:5 | 1:10 | 1:20 | 1:30 | 1:50 |
|---|---|---|---|---|---|---|---|
| 700 bp | 492.4 | 475.7 | 489.3 | 338.7 | 143.6 | 58.54 | — |

Example 7

Doubling the Injection Events Enhanced the dsRNA Silencing Effect

Figure 8B:
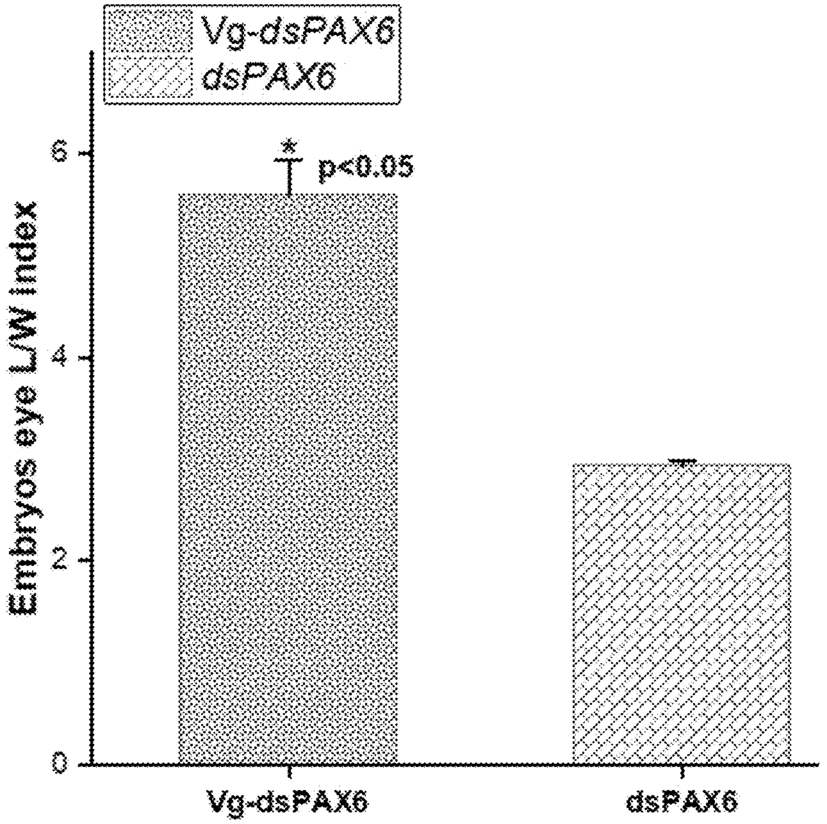
Figure 8C:
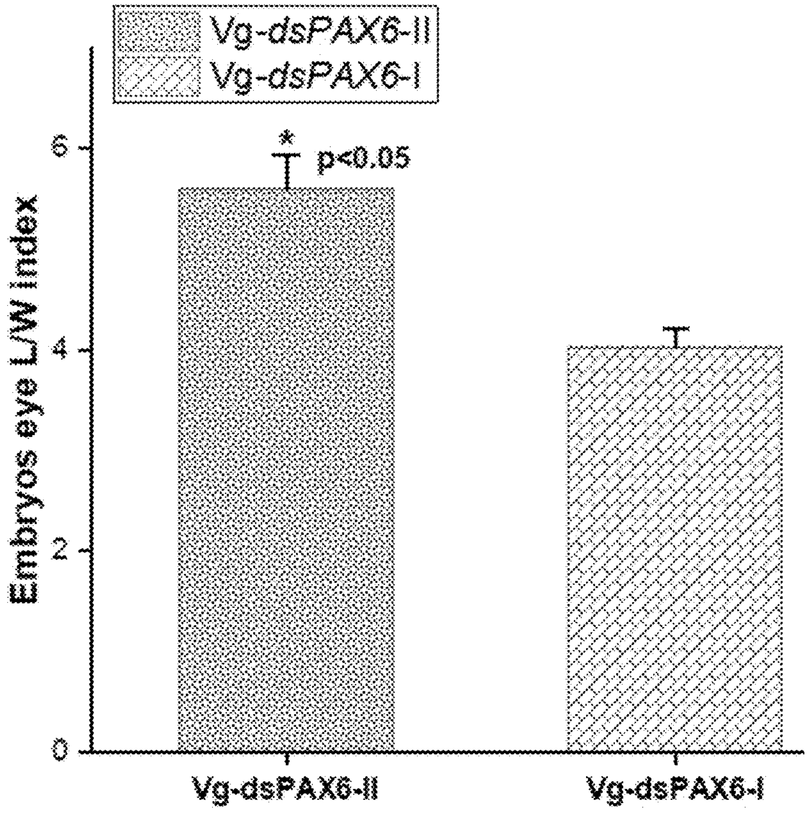

To the vitellogenesis-induced females (details in material and methods), KH9-Vg peptide conjugated to dsPAX6 or solo dsPAX6 were injected in greater dosage than previous experiment (4 µg of each dsPAX6A and B/gr body weight, peptide: dsPAX6 5:1 molar ratio). Upon egg laying, the embryos development on the pleopods of the treated mother were monitored for eye development. The eyes of 60% of the embryos taken from Vg-dsPAX6 injected females represent irregular development (FIGS. 8A-I to 8A-III). The length/width index average of the eye line of 10 days old embryos taken from Vg-dsPAX6 injected mother was 5.6±0.37 (FIG. 8A-III), a significantly greater index compared to the eye of the control group (2.94±0.05) (FIG. 8B). Comparing the length/width index of the eye line obtained from the two separated experiments indicates that the index of the previous experiment was significantly lower (4.03±0.18) than the eye index obtained from the current experiment (FIG. 8C). The latter indicates that a greater dose, in a vitellogenesis induced female could provide greater silencing efficiency, and therefore, significantly retarded eye development, in the case of PAX6 silencing.

Example 8

Long-Term Effect of PAX6 Silencing Via Vg-Peptide Delivery

To test whether early stages of silencing targeting a developmental gene such as PAX6 influence later developmental stages, e.g., 10th and 11th stage larvae (from higher dosage injection experiment) were taken for 3D eye surface analysis by scanning electron microscope (SEM). SEM analysis revealed deformed ommatids shape in the experiment larvae. While the control larvae (FIGS. 9A-I to 9A-III)

demonstrated well shaped hexagonal ommatids, the experimental group larvae's ommatids exhibited irregular, elongated, continuous or elevated hinges between ommatids (FIGS. 9B-I to 9C-III).

Example 9

Developing a Delivery Tool for CRISPR-Cas9

Figure 10B:
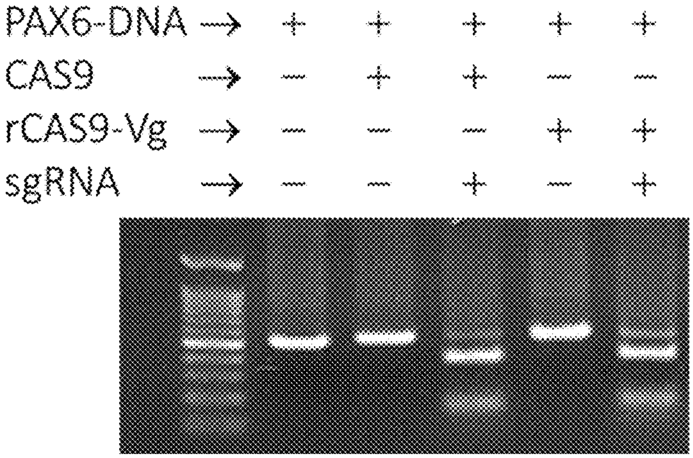
Figure 10C:
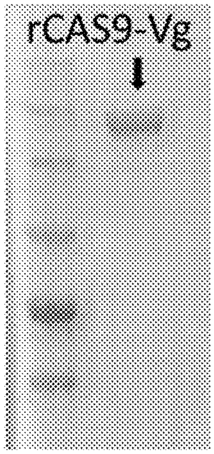
Figure 10D:
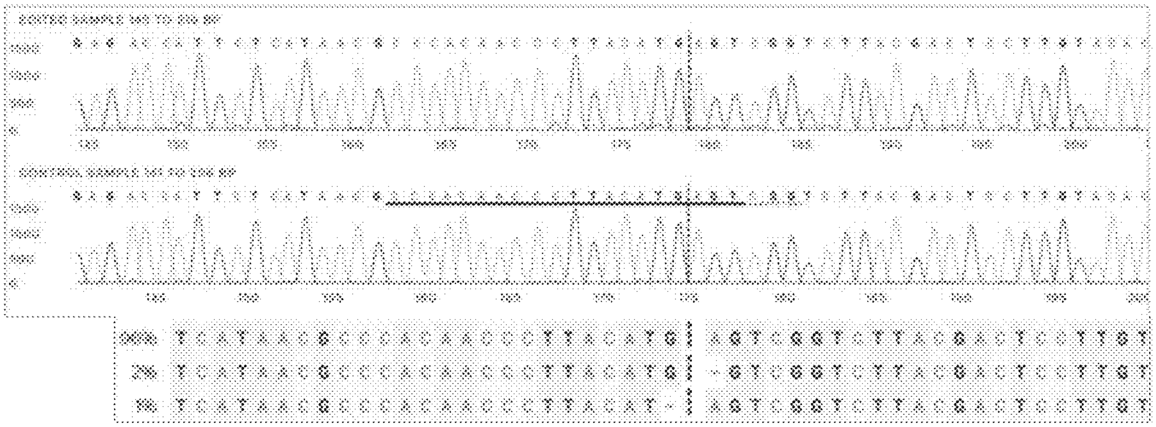
Figure 10E:
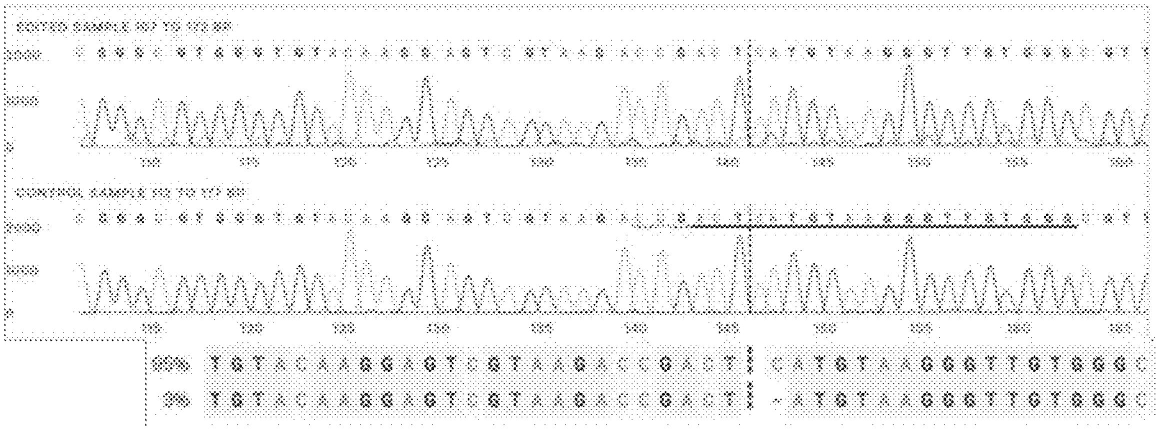

As indicated earlier, dsRNA silencing with Vg-dsRNA conjugate affected about 60% of the embryos. dsRNA is used for short term silencing, therefore, and shortly after dsRNA treatment the effect is halted. For long-term gene editing or knockout, recombinant Vg-peptide fused to Cas9 was designed. This complex contained His ×6, VgR interacting domain of 84 amino acid sequence derived from vitellogenin and CAS9 sequence (FIG. 10A). 3D prediction of the hybrid protein indicated that the Vg derived peptide is arranged as a random coil and β-sheet structures (FIG. 10A). The construct His-tagged Cas9.Vg was cloned into PET28A plasmid and expressed in *E-coli* BL21. The expressed recombinant protein Cas9-Vg-His was purified on Ni-NTA, followed by ion exchange column, thereafter, the elution fractions were separated on SDS-PAGE (FIG. 10C). A clear thick band of the purified Cas9-Vg protein was observed in the SDS-PAGE (FIG. 10C). Mass spectrometry (MS) analysis confirmed that the Coomassie blue stained band observed at ~160 kDa was indeed CAs9 fused to Vg. The activity of Cas9 was tested. The Cas9-Vg complex showed DNA cleaving activity only when mixed with specific gRNA (FIG. 10B). Incubating the Cas9-Vg with specific gRNA complementary to PAX6 560 bp cDNA lead to the cleavage of the latter to smaller fragments, e.g., 460 bp and 100 bp. Cas9-Vg without gRNA did not cleave the DNA. Further, the cleaving activity appeared to be similar to the activity of a commercial Cas9 (FIG. 10B). Thereafter, Cas9-Vg was mixed with the PAX6 gRNA and the mixture was injected into vitellogenic females. Ten (10) days after spawning, several embryos were collected, and their DNA was extracted. Indeed, the inventors have shown that a gene editing event has occurred (FIGS. 10D-10E). FIGS. 10D-10E represent the newly appeared different small peaks in addition to the original peaks in the sequence of the forward template (FIG. 10D) and the reverse template (FIG. 10E) of the Sanger chromatogram. The chromatogram depicts the occurrence of single nucleotide deletion in PAX6 gene at the 4th upstream position of PAM, indicating that the gene encoding PAX6 was edited in the embryos.

Example 10

Internalization of Vg-Derived Peptides into Decapod Oocytes

The inventors further examined the capability and efficacy of shorter/partial sequences derived from the peptide of the invention to being internalized into *M. rosenbergii* oocytes. Further, the inventors examined whether homologous peptides derived from a different decapod crustacean, e.g., Litopenaeus vannamei, would also be internalized into *M. rosenbergii* oocytes.

TABLE 4

Custom peptides designed to evaluate minimal peptide length and *L. vannamei* peptides capable of being internalized into *M. rosenbergii* oocytes

| Peptide ID | Amino acid sequence |
|---|---|
| Vg237-244-TAMRA | DKNIIKPK-TAMRA (SEQ ID NO: 37) |
| Vg246-253-TAMRA | GSYKYVEAK-TAMRA (SEQ ID NO: 38) |
| Vg237-253-TAMRA | DKNIIKPAYGSYKYVEAK-TAMRA (SEQ ID NO: 39) |
| VgVa238-245-TAMRA | DKNIVRPAK-TAMRA (SEQ ID NO: 40) |
| VgVa248-254-TAMRA | GIYKYVEAK-TAMRA (SEQ ID NO: 41) |

The mentioned peptides were incubated in vitro with ovary slices to evaluate their internalization. The scVg-FITC peptide, used as control, was observed only on the outer area of the oocyte, around and above follicular cells (FIGS. 11B-11G). In contrast to that, the Vg-derived peptides were capable to enter the oocyte as they were observed beyond the follicular cells inside the oocytes (red dots, FIGS. 11B-11G). Weaker florescent intensity was observed when Vg235-260-TAMRA, Vg237-244-TAMRA, Vg237-253-TAMRA (FIGS. 11B-11D) were used, compared to the intensity obtained when Vg246-253-TAMRA peptide was used (FIG. 11E). Moreover, both L. vannamei Vg derived peptides were capable to endocytose into *M. rosenbergii* oocytes (FIGS. 11F-11G).

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A chimera comprising a peptide comprising the amino acid sequence of KHKHKHKHKHKHKHKHKHKH-CDKNIIKPAYGSYKYVEAHQESVLRK (SEQ ID NO: 24) directly or indirectly bound to a double stranded RNA (dsRNA) molecule, wherein the molar ratio of dsRNA: peptide is 1:5 to 1:20 therefor.

2. The chimera of claim 1, wherein said peptide and said dsRNA molecule are non-covalently bound.

3. A composition comprising the chimera of claim 1, and a carrier.

4. A method for making the chimera of claim 1, comprising binding said peptide to said dsRNA molecule.

5. A method for: (i) delivering a dsRNA molecule into a cell; or (ii) modifying a cell, comprising contacting said cell with the chimera of claim 1, thereby (i) delivering said dsRNA molecule into the cell; or (ii) modifying said cell.

6. The method of claim 5, wherein said cell is a cell of an oviparous animal.

7. A chimera comprising a first peptide comprising the amino acid sequence:

KHKHKHKHKHKHKHKHKHKHCDKNIIKPAYGSY-KYVEAHQESVLRK (SEQ ID NO: 24) directly or indirectly bound to an agent selected from the group consisting of: polynucleotide, a second peptide, a small molecule, or any combination thereof.

* * * * *